United States Patent
Szardenings et al.

(10) Patent No.: US 10,400,234 B2
(45) Date of Patent: Sep. 3, 2019

(54) PHAGE DISPLAY LIBRARY

(71) Applicant: Fraunhofer-Gesellschaft zur Foerderung der angewandten Forschung e.V., Munich (DE)

(72) Inventors: Michael Szardenings, Leipzig (DE); Nicolas Delaroque, Leipzig (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 20 days.

(21) Appl. No.: 15/307,480

(22) PCT Filed: Mar. 27, 2015

(86) PCT No.: PCT/EP2015/056677
§ 371 (c)(1),
(2) Date: Oct. 28, 2016

(87) PCT Pub. No.: WO2015/165667
PCT Pub. Date: Nov. 5, 2015

(65) Prior Publication Data
US 2017/0058276 A1 Mar. 2, 2017

(30) Foreign Application Priority Data
Apr. 30, 2014 (EP) .................................... 14166662

(51) Int. Cl.
C12N 15/10 (2006.01)
(52) U.S. Cl.
CPC ................ C12N 15/1037 (2013.01)
(58) Field of Classification Search
None
See application file for complete search history.

(56) References Cited

FOREIGN PATENT DOCUMENTS

| WO | 1998033901 A1 | 8/1998 |
|----|---------------|--------|
| WO | 2000077194 A1 | 12/2000 |

OTHER PUBLICATIONS

Collins et al. Reviews in Molecular Biotechnology 74.4 (2001): 317-338. (Year: 2001).*
Kügler et al. (Journal of Biological Chemistry 287.46 (2012): 39224-39232.) (Year: 2012).*
Bossi, "Context effects: Translation of UAG codon by suppressor tRNA is affected by the sequence following UAG in the message", Feb. 15, 1983, pp. 73-87, vol. 164, No. 1, Publisher: Journal of Molecular Biology.
Collins, et al., "Cosmix-plexing: a novel recombinatorial approach for evolutionary selection from combinatorial libraries", Jan. 1, 2001, pp. 317-338, vol. 74, No. 4, Publisher: Reviews in Molecular Biotechno.
Dennis, et al., "Albumin binding as a general strategy for improving the pharmacokinetics of proteins", Sep. 20, 2002, pp. 35035-35043, vol. 277, No. 38, Publisher: J Biol Chem.
Devlin, et al., "Random Peptide Libraries: a Source of Specific Protein Binding Molecules", Jul. 27, 1990, pp. 404-406, vol. 249, Publisher: Science.
Dias-Neto, et al., "Next-generation phage display: integrating and comparing available molecular tools to enable cost-effective high-throughput analysis", Dec. 17, 2009, p. E8338, vol. 4, No. 12, Publisher: PLOS ONE.
Extended European Search Report received in EP 14166662.8 dated Nov. 5, 2014.
Giebel, et al., "Screening of cyclic peptide phage libraries identifies ligands that bind strepavidin with high affinities", Nov. 1, 1995, p. 1530 15435, vol. 34, Publisher: Biochemistry.
Hoen, et al., "Phage display screening without repetitious selection rounds", Feb. 1, 2012, pp. 622-631, vol. 421, No. 2, Publisher: Analytical Biochemistry.
Koivunen, et al., "Phage Libraries Displaying Cyclic Peptides with Different Ring Sizes: Ligand Specificities of the RDG-Directed Integrins", Mar. 1, 1995, pp. 265-270, vol. 13, No. 3, Publisher: Biotechnology. The International Monthly for Industrial Biology.
McConnel, et al., "Isolation of Erythropoietin Receptor Agonist Peptides Using Evolved Phage Libraries", Oct. 1, 1998, pp. 1279-1286, vol. 379, Publisher: Biological Chemistry.
Metzker, et al., "Emerging Technologies in DNA Sequencing", Dec. 1, 2005, pp. 1767-1776, vol. 15, No. 12, Publisher: Genome Research.
http://www.cosmix.de/menu2.htm, Aug. 13, 1998.
Santoso, et al., "simple and efficient maleimide-based approach for peptide extension with a cysteine-containing peptide phage library", Aug. 13, 2013, p. 5680 5683, vol. 23, Publisher: Bioorganic & Medicinal Chemistry Letters.

(Continued)

Primary Examiner — Tracy Vivlemore
Assistant Examiner — Sahana S Kaup
(74) Attorney, Agent, or Firm — Suzannah K. Sundby, Esq.; Canady + Lortz LLP

(57) ABSTRACT

A library of replicating entities, each entity comprises a recombinant vector comprising a randomized nucleic acid sequence, having the reading frame structure $[NXX]_n$ $[CorAA]$ $[NXX]_m$ $[NZZ]_o$, or $[NZZ]_o$ $[NXX]_m$ $[CorAA]$ $[NXX]_n$. Each NXX is independently a codon encoding for any amino acid except cysteine, CorAA is a codon encoding for cysteine or at least one other amino acid, each NZZ is independently a codon encoding for any amino acid, and n is an integer from 0 to 40, m is an integer from 1 to 20, o is an integer from 1 to 40, and at least 20 percent of CorAA encode for cysteine. The invention further relates to a set of recombinant vectors and to a set of randomized oligonucleotides, each oligonucleotide having said structure, as well as to a method for generating a library of replicating entities and to a method for identifying an amino acid polymer.

17 Claims, 6 Drawing Sheets
Specification includes a Sequence Listing.

(56) References Cited

OTHER PUBLICATIONS

Sidhu, et al., "Phage Display for Selection of Novel Binding Peptides", Jan. 1, 2000, pp. 333-363, vol. 328, Publisher: Methods in Enzymology.

Srila, et al., "Identification of amino acid residues responsible for the binding to anti-FLAGTM M2 antibody using a phage display combinatorial peptide library", Oct. 1, 2013, pp. 583-589, vol. 171, No. 3, Publisher: Appl Biochem Biotechnol.

Szardenings, et al., "A phasmid optimised for protein design projects: pMAMPF", Sep. 28, 1990, pp. 1-7, vol. 94, No. 1, Publisher: Gene.

Uchiyama, et al., "Designing scaffolds of peptides for phage display libraries", May 1, 2005, pp. 448-456, vol. 99, No. 5, Publisher: Journal of Bioscience and Bioengineering.

Van Den Brulle, et al., "A novel solid phase technology for high-throughput gene synthesis", Sep. 1, 2008, pp. 340-343, vol. 45, No. 3, Publisher: Biotechniques Rapid Dispatches.

Wright, et al., "Binding epitope of somatostatin defined by phage-displayed peptide libraries", Feb. 1, 1995, p. 165 169, vol. 13, Publisher: Biotechnology.

\* cited by examiner

```
        BsgI                              BpmI            BstXI  KpnI
·ValValGlnAlaGlyAxxAxxAxxCysAxxAxxAxxAxxAxxAxxAaaAaaAaaAaaAmcSerSerProValGlyThrAla
                         Ser

CGTAGTGCAGGCCGGCN##N##N+ +TSCN##N##N##N##NZZNYYNZZNZZNNCTCCAGCCCAGTGGGTACCGCTG
GCATCACGTCCGGCCGN##N##N##N++AWGN##N##N##N##NZZNYYNZZNZZNNGAGGTCGGGTCACCCATGGCGAC (SEQ ID NOs.: 41, 42, 43)

NYY: any codon ending on certain non palindromic NN
NZZ: any codon (no Trp no Met)
N##: any codon (no Cys no Met)
N++: any codon MUST end with a K, NO Cys
NNC: any codon ending on C
(or NNK instead of N++)
```

Figure 2

| Amino acid | 1 | 2 | 3 | 4 | 5 | 6 | 7 | 8 | 9 | 10 |
|---|---|---|---|---|---|---|---|---|---|---|
| A | 0 | 14223 | 30764 | 59520 | 0 | 34979 | 34927 | 35957 | 37340 | 45882 |
| C | 0 | 0 | 0 | 0 | 0 | 0 | 0 | 0 | 0 | 52739 |
| D | 0 | 39553 | 48875 | 0 | 542879 | 0 | 0 | 0 | 0 | 43559 |
| E | 0 | 87276 | 75249 | 0 | 0 | 44237 | 43152 | 43960 | 44414 | 61686 |
| F | 0 | 27597 | 31717 | 42366 | 0 | 66307 | 62500 | 60241 | 63183 | 44711 |
| G | 890098 | 39474 | 34093 | 41077 | 0 | 39638 | 44928 | 41682 | 41101 | 37590 |
| H | 0 | 75894 | 73003 | 98515 | 0 | 34497 | 32948 | 35835 | 36645 | 72643 |
| I | 0 | 83439 | 54740 | 0 | 0 | 71897 | 70817 | 72014 | 72882 | 41349 |
| K | 0 | 42765 | 41121 | 0 | 0 | 56178 | 47634 | 45037 | 45853 | 32693 |
| L | 0 | 28249 | 31078 | 44758 | 0 | 39457 | 34728 | 31923 | 32861 | 40015 |
| M | 0 | 0 | 0 | 73416 | 0 | 32513 | 37952 | 38648 | 37336 | 0 |
| N | 0 | 78344 | 63037 | 72334 | 0 | 62659 | 55267 | 52492 | 51546 | 37204 |
| P | 0 | 46507 | 51343 | 62913 | 347219 | 43711 | 49739 | 49377 | 51325 | 49671 |
| Q | 0 | 68512 | 68646 | 107341 | 0 | 69027 | 75093 | 77506 | 74916 | 75704 |
| R | 0 | 23590 | 35128 | 51444 | 0 | 34695 | 36485 | 39342 | 39704 | 40246 |
| S | 0 | 32265 | 37367 | 47980 | 0 | 35020 | 41584 | 40643 | 39856 | 43980 |
| T | 0 | 44732 | 45182 | 57546 | 0 | 46996 | 43576 | 43289 | 42170 | 42192 |
| V | 0 | 75176 | 69694 | 76262 | 0 | 70726 | 65238 | 65776 | 67238 | 69886 |
| W | 0 | 30047 | 41143 | 54626 | 0 | 49821 | 55649 | 58697 | 53877 | 0 |
| Y | 0 | 52455 | 57918 | 0 | 0 | 57740 | 57881 | 57679 | 57851 | 58348 |

Library insert position

Figure 3

| Amino acid | 11 | 12 | 13 | 14 | 15 | 16 | 17 | 18 | 19 | 20 |
|---|---|---|---|---|---|---|---|---|---|---|
| A | 47333 | 0 | 38251 | 47474 | 50664 | 53781 | 33 | 0 | 0 | 0 |
| C | 52814 | 103565 | 46688 | 57993 | 57768 | 58026 | 190795 | 0 | 0 | 0 |
| D | 43881 | 0 | 41465 | 38896 | 39939 | 30386 | 125084 | 0 | 0 | 0 |
| E | 65096 | 127439 | 58659 | 54857 | 54353 | 53113 | 35 | 0 | 0 | 0 |
| F | 44367 | 0 | 44566 | 49897 | 48641 | 47357 | 177519 | 0 | 0 | 0 |
| G | 41350 | 72717 | 36293 | 33244 | 32059 | 36307 | 12 | 0 | 0 | 890098 |
| H | 72477 | 0 | 79809 | 73568 | 71763 | 71739 | 50 | 0 | 0 | 0 |
| I | 42835 | 57154 | 43434 | 42321 | 41949 | 40110 | 116798 | 0 | 0 | 0 |
| K | 34764 | 53551 | 33243 | 29846 | 28429 | 25919 | 21 | 0 | 0 | 0 |
| L | 37956 | 0 | 44064 | 42561 | 42391 | 45245 | 18 | 0 | 0 | 0 |
| M | 0 | 0 | 0 | 0 | 0 | 0 | 0 | 0 | 0 | 0 |
| N | 36289 | 0 | 36456 | 35383 | 35904 | 34590 | 81881 | 0 | 0 | 0 |
| P | 47257 | 88645 | 53991 | 47098 | 46903 | 47226 | 6 | 0 | 0 | 0 |
| Q | 70121 | 146239 | 80952 | 75267 | 76779 | 77028 | 8 | 0 | 0 | 0 |
| R | 40027 | 62288 | 42228 | 41372 | 40497 | 44503 | 0 | 0 | 0 | 0 |
| S | 41643 | 0 | 43382 | 46464 | 45494 | 45935 | 13 | 0 | 890098 | 0 |
| T | 41484 | 0 | 43723 | 42696 | 43877 | 45877 | 10 | 890098 | 0 | 0 |
| V | 73886 | 0 | 67274 | 69426 | 70825 | 70503 | 16 | 0 | 0 | 0 |
| W | 0 | 92899 | 0 | 0 | 0 | 0 | 0 | 0 | 0 | 0 |
| Y | 56518 | 85501 | 55620 | 61735 | 61863 | 62453 | 197799 | 0 | 0 | 0 |

Library insert position

Figure 3 (continued)

PHAGE DISPLAY LIBRARY

REFERENCE TO A SEQUENCE LISTING

The content of the ASCII text file of the sequence listing submitted to the European Patent Office on Mar. 27, 2015, which forms part of the description of PCT/EP2015/056677 is incorporated herein by reference in its entirety.

FIELD OF THE INVENTION

The invention relates to a library of replicating entities, each entity comprises a recombinant vector comprising a randomized nucleic acid sequence, having the reading frame structure $[NXX]_n$ $[CorAA]$ $[NXX]_m$ $[NZZ]_o$, or $[NZZ]_o$ $[NXX]_m$ $[CorAA]$ $[NXX]_n$. The invention further relates to a set of recombinant vectors, each vector comprises a randomized nucleic acid sequence, having said reading frame structure and to a set of randomized oligonucleotides, each oligonucleotide having said structure. Furthermore, the invention relates to a method for generating a library of replicating entities and to a method for identifying an amino acid polymer.

BACKGROUND OF THE INVENTION

Libraries of genes, small molecules, proteins or peptides are nowadays widely used for identifying novel compounds of particular pharmacological or chemical properties. One of the most successful strategies for identifying ligands from large biological libraries is the phage display method, which was developed more than 25 years ago. Following the first antibody libraries, random peptide libraries based on phage display were developed. Finally, screening approaches based on the concept of phage display libraries have also been introduced for eukaryotic cells, in particular yeast, but also for cells of higher organisms.

Despite several improvements of the techniques, screening results from such random peptide libraries are still not fully satisfying. In general, all approaches are based on randomly generated nucleic acid sequences, which are translated into a peptide within an organism, such that the library, at best, covers all possible variants of a peptide of a given length. However, as randomization is carried out on the level of the encoding nucleic acid sequence, already the number of nucleic acid sequences covering all possible variants of a peptide of only eight amino acids exceeds the size of a library that can be technically handled.

Moreover, the binding affinities of a peptide distinctly depend on its three-dimensional structure. As a consequence, many targets are bound by circular but not by linear peptides of corresponding sequences. Other targets, in contrast, are exclusively bound by linear peptides. Although ordinary peptide gene libraries theoretically include appropriate loops, their complexity is simply too small to cover the theoretically required amount of sequences. To address this problem, most screenings are performed using at least two different libraries, one including peptides that have been cyclised by including defined positions with codons for cysteines at or near the N- and C-terminus of the peptide. These cysteine residues can form a disulfide bond generating a loop structure. The use of several libraries is, however, time consuming and extremely elaborate, especially as most targets are either bound by linear peptides or by circular peptides.

Therefore, novel gene libraries are needed, which cover circular and linear versions of peptides alike with a reasonably high probability.

SUMMARY OF THE INVENTION

In a first aspect, the invention relates to a library of replicating entities, each entity comprises a recombinant vector comprising a randomized nucleic acid sequence, having the reading frame structure $[NXX]_n$ $[CorAA]$ $[NXX]_m$ $[NZZ]_o$ or $[NZZ]_o$ $[NXX]_m$ $[CorAA]$ $[NXX]_n$ wherein each NXX is independently a codon encoding for any amino acid except cysteine, CorAA is a codon encoding for cysteine or at least one other amino acid, each NZZ is independently a codon encoding for any amino acid, and n is an integer from 0 to 40, m is an integer from 1 to 20, o is an integer from 1 to 40, and at least 20 percent of CorAA encode for cysteine.

In a further aspect, the invention relates to a set of recombinant vectors, each vector comprises a randomized nucleic acid sequence, having the reading frame structure $[NXX]_n$ $[CorAA]$ $[NXX]_m$ $[NZZ]_o$, or $[NZZ]_o$ $[NXX]_m$ $[CorAA]$ $[NXX]_n$ wherein each NXX is independently a codon encoding for any amino acid except cysteine, CorAA is a codon encoding for cysteine or at least one other amino acid, each NZZ is independently a codon encoding for any amino acid, and n is an integer from 0 to 40, m is an integer from 1 to 20, o is an integer from 1 to 40, and at least 20 percent of CorAA encode for cysteine.

In a further aspect, the invention relates to a set of randomized oligonucleotides, each oligonucleotide having the structure $[NXX]_n$ $[CorAA]$ $[NXX]_m$ $[NZZ]_o$, or $[NZZ]_o$ $[NXX]_m$ $[CorAA]$ $[NXX]_n$ wherein each NXX is independently a codon encoding for any amino acid except cysteine, CorAA is a codon encoding for cysteine or at least one other amino acid, each NZZ is independently a codon encoding for any amino acid, and n is an integer from 0 to 40, m is an integer from 1 to 20, o is an integer from 1 to 40, and at least 20 percent of CorAA encode for cysteine.

In a further aspect, the invention relates to a method for generating a library of replicating entities comprising the steps providing a set of randomized oligonucleotides of the invention, introducing each oligonucleotide into a replicating entity, and propagating the replicating entities as individual clones.

In a further aspect, the invention relates to a method for identifying an amino acid polymer able to interact with a target, comprising the steps providing a library of replicating entities of the invention, bringing the library into contact with the target, and enriching the replicating entities interacting with the target.

In a further aspect, the invention relates to the use of a set of randomized oligonucleotides of the invention for generating a library of replicating entities.

BRIEF DESCRIPTION OF THE DRAWINGS

FIG. 2 shows the reading frame structure of the phage display library ENTE-1 including restriction sites and codon restrictions.

FIG. 3 shows the distribution of amino acids at each position of the library ENTE-1.

DETAILED DESCRIPTION OF THE INVENTION

Figure 1:
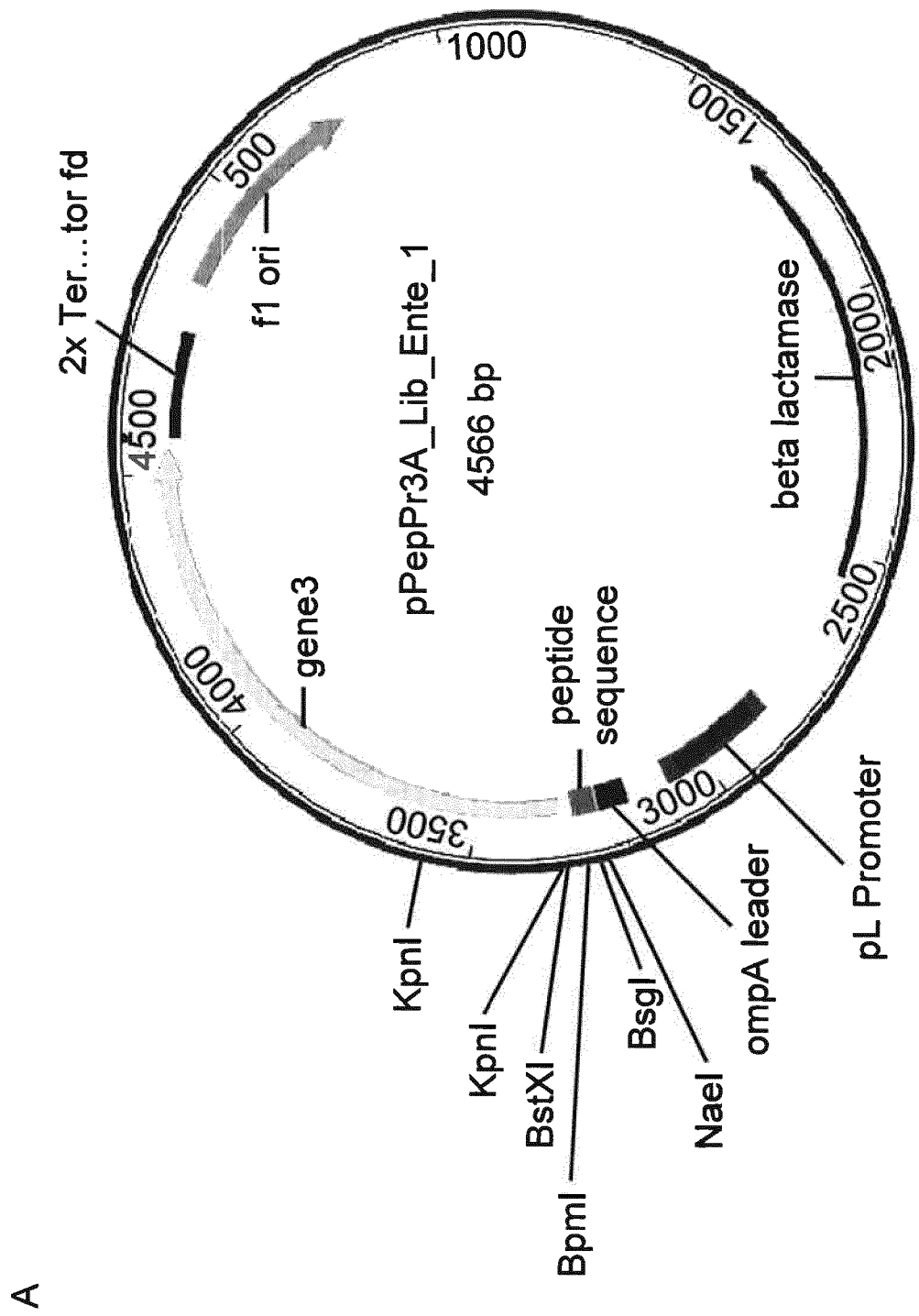
FIG. 1 shows a schematic drawing of the vectors pPepPr3A-stuffer (A) and pPepPr7B-stuffer (B) used to generate the phage display libraries ENTE-1 and ENTE-2, respectively.
Figure 1:
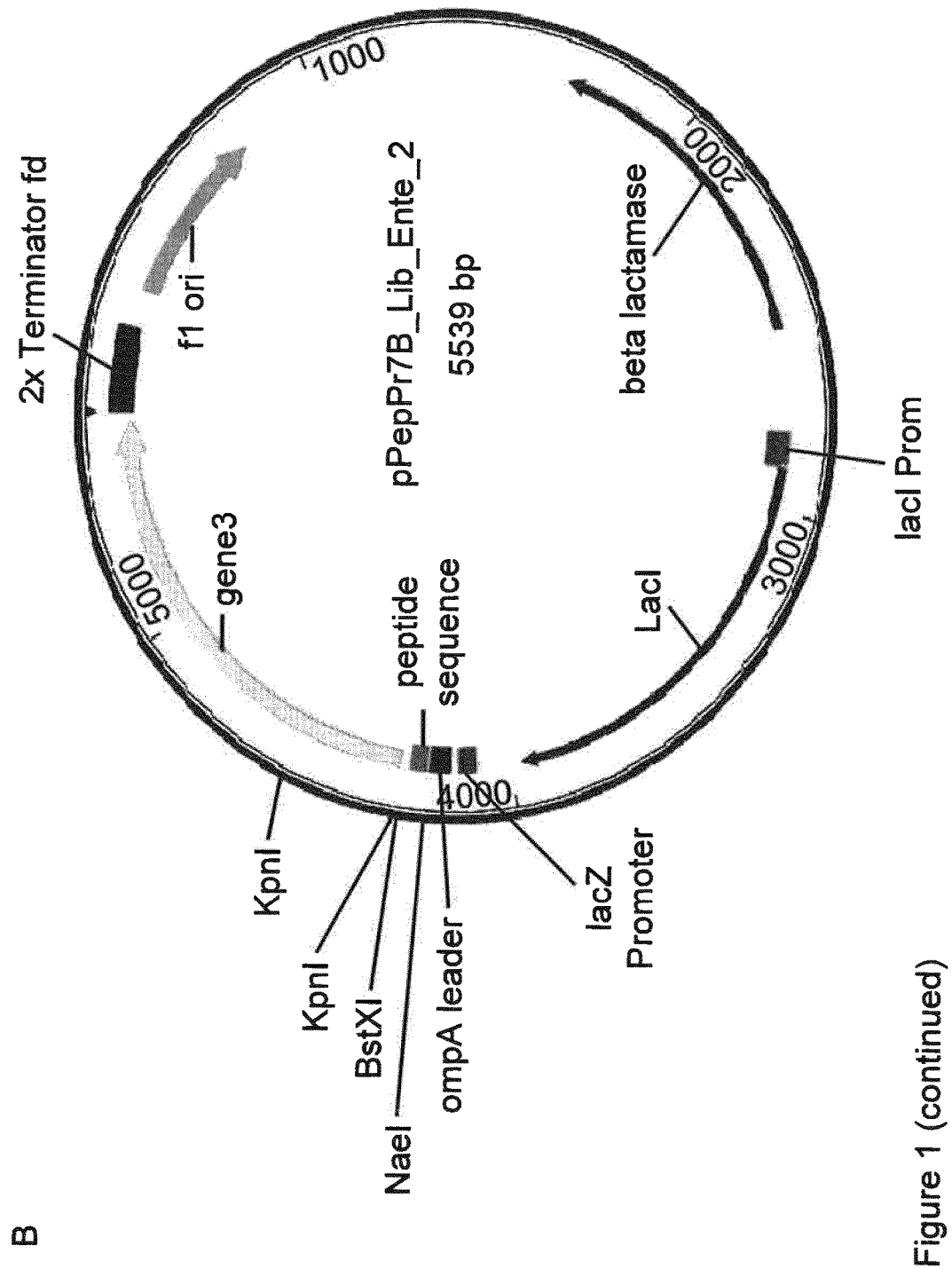

In a first aspect, the invention relates to a library of replicating entities, each entity comprises a recombinant vector comprising a randomized nucleic acid sequence, having the reading frame structure $[NXX]_n$ $[CorAA]$ $[NXX]_m$ $[NZZ]_o$, or $[NZZ]_o$ $[NXX]_m$ $[CorAA]$ $[NXX]_n$ wherein each NXX is independently a codon encoding for any amino acid except cysteine, CorAA is a codon encoding for cysteine or at least one other amino acid, each NZZ is independently a codon encoding for any amino acid, and n is an integer from 0 to 40, m is an integer from 1 to 20, o is an integer from 1 to 40, and at least 20 percent of CorAA encode for cysteine.

The library of the invention is characterized in that the replicating entities encode for a large variety of peptides (also referred to as amino acid polymers), wherein the peptides are represented in a linear version and in a circular version. This is achieved by the specific structure of the reading frame of the nucleic acid sequence encoding for the peptide. In general, the nucleic acid sequence comprises two different parts, namely $[NXX]_n$ $[CorAA]$ $[NXX]_m$ and $[NZZ]_o$. The part $[NXX]_n$ $[CorAA]$ $[NXX]_m$ comprises at least two amino acids (n=0; m=1), of which no more than one amino acid (namely the one encoded by CorAA) may be a cysteine. The $[NZZ]_o$ part consist of up to 40 amino acids and may comprise any combination of amino acids including cysteine. Besides the one position CorAA, which is occupied by a cysteine (C) in at least 20 percent of the nucleic acid sequences, all other codons are randomized. Thus, each NXX independently may be any codon encoding for an amino acid except cysteine and each NZZ independently may be any codon encoding for an amino acid. In other words, each NXX and each NZZ may be independently selected from codons listed in Table 1. Preferably, the codons encode for natural amino acids. However, one or more codons may encode for non-natural amino acids, when the library is generated using replicating entities or hosts of replicating entities, which are provided with tRNA molecules transferring non-natural amino acids.

TABLE 1

Codons and encoded amino acids

| Group | Codon | Encoded natural amino acid |
| --- | --- | --- |
| 1 | GCT, GCC, GCA, GCG | Alanine |
| 2 | TTA, TTG, CTT, CTC, CTA, CTG, | Leucine |
| 3 | CGT, CGC, CGA, CGG, AGA, AGG, | Arginine |
| 4 | AAA, AAG | Lysine |
| 5 | AAT, AAC | Asparagine |
| 6 | ATG | Methionine |
| 7 | GAT, GAC | Aspartic acid |
| 8 | TTT, TTC | Phenylalanine |
| 9 | CCT, CCC, CCA, CCG | Proline |
| 10 | CAA, CAG | Glutamine |
| 11 | TCT, TCC, TCA, TCG, AGT, AGC, | Serine |
| 12 | GAA, GAG | Glutamic acid |
| 13 | ACT, ACC, ACA, ACG | Threonine |
| 14 | GGT, GGC, GGA, GGG | Glycine |
| 15 | TGG | Tryptophane |
| 16 | CAT, CAC | Histidine |
| 17 | TAT, TAC | Tyrosine |

TABLE 1-continued

Codons and encoded amino acids

| Group | Codon | Encoded natural amino acid |
| --- | --- | --- |
| 18 | ATT, ATC, ATA | Isoleucine |
| 19 | GTT, GTC, GTA, GTG | Valine |
| 20 | TGT, TGC | Cysteine* |

*only for NZZ; In case of ribonucleic acid, thymine may be replaced by uracile.

In case the position CorAA is occupied by a codon encoding for cysteine and the part $[NZZ]_o$ of the nucleic acid sequence also comprises a codon encoding for cysteine, the resulting peptide will comprise two cysteines, which form a disulfide bond. This results in a circular version of the peptide. Moreover, due to the exclusion of cysteine from NXX, the occurrence of two closely adjacent cysteine residues in the $[NXX]_n$ $[CorAA]$ $[NXX]_m$ part is avoided. This is advantageous, because two adjacent cysteines would both be able to form a disulfide-bond with a cysteine of the $[NZZ]_o$ part, resulting in a nucleic acid sequence that encodes for two peptides of identical sequence, however, different conformation. Thus, restricting the number of cysteines in the $[NXX]_n$ $[CorAA]$ $[NXX]_m$ part significantly improves the reliability of the library. Moreover, in contrast to usual cysteine constrained libraries, which carry a cysteine at each side of the randomized peptide, the library of the invention encodes for peptides having loops of different sizes, as the cysteine may be localized at any position.

Furthermore, due to its reading frame structure, the library of the invention provides the randomized peptides as a circular and a linear version. Namely, corresponding to a nucleic acid sequence encoding for a peptide having a cysteine at the CorAA position, the library also comprises a nucleic acid sequence encoding for a peptide, in which the CorAA position is occupied by a specific amino acid, other than cysteine. Additionally, at least 20 percent of the CorAA codons encode for cysteine. This is much more than in a standard randomized library. As a result, at least 20 percent of the replicating entities comprise a recombinant vector comprising a randomized nucleic acid sequence in which CorAA is a codon encoding for cysteine. Importantly, the peptides encoded by a randomized nucleic acid sequence with CorAA encoding for cysteine will form a disulfide bond, if a further cysteine is contained in the $[NZZ]_o$ part. Corresponding peptides of identical sequence but with CorAA encoding for a different amino acid will remain linear. Thus, by the reading frame structure of the library, corresponding linear and circular peptides are covered by a single library. Additionally, by defining the position and probability of a cysteine in one part of the encoded peptide (namely the $[NXX]_n$ $[CorAA]$ $[NXX]_m$ part), the probability of a disulfide-bond within the peptide is specified. This results in a high statistical reliability of the library. Accordingly, a library of replicating entities is generated, in which each entity comprises a peptide, preferably presented on its surface. The peptides have the common structure of $X_n$ C/AA $X_m$ $Z_o$, with X being any amino acid except cysteine, C/AA being cysteine or at least one other amino acid and Z being any amino acid. Additionally, n is an integer from 0 to 40, m is an integer from 1 to 20, o is an integer from 1 to 40, and in at least 20 percent of the peptides C/AA is cysteine.

An exemplary library may comprise a first set of replicating entities, each entity comprising a recombinant vector with a randomized nucleic acid sequence, having the reading frame structure $[NXX]_n$ $[TGY]$ $[NXX]_m$ $[NZZ]_o$, and a second set of replicating entities, each entity comprising a recombinant vector with a randomized nucleic acid sequence, having the reading frame structure $[NXX]_n$ [TCN] $[NXX]_m$ $[NZZ]_o$, wherein the first set of replicating entities constitute at least 20 percent of the library. In this case, each NXX individually represents a codon encoding for any amino acid except cysteine, TGY represents a codon encoding for cysteine, TCN represents a codon encoding for serine, and each NZZ individually represents a codon encoding for any amino acid. Additionally, m is an integer from 0 to 40, n is an integer from 1 to 20, and o is an integer from 1 to 40.

In a preferred embodiment, the replicating entity is a cell or a virus, preferably the cell is a prokaryotic cell or a eukaryotic cell and/or the virus is a bacteriophage. The term "library" as used herein refers to a compilation of a large number of specimens, i.e. replicating entities, of the same kind, however, differing from each other such that the library covers a large variety of the respective specimen. Preferably, the library is formed by cells or viruses carrying DNA or RNA such that the replicating entity can translate the encoded peptide either itself (in case of a cell) or by means of a host (in case of a virus). Virus-based libraries of randomized peptides such as phage display libraries are well established and widely used. Accordingly, in a preferred embodiment, the library is a phage display library, preferably the phage is a filamentous phage. In a preferred embodiment, the phage is selected from the group consisting of M13, fd, fl, T and λ-phage.

In addition to the well established technology of phage display libraries, cell-based libraries become increasingly important, in particular libraries based on bacteria or yeast but also based on fungi. The reading frame structure is likewise suitable for such libraries.

In a preferred embodiment, CorAA is a codon encoding for cysteine or 1 to 5 other amino acids, preferably 1 to 3 other amino acids, more preferred one other amino acid. To cover corresponding linear and circular peptides, the position CorAA within the $[NXX]_n$ [CorAA] $[NXX]_m$ part of the nucleic acid sequence is occupied by either cysteine (allowing a loop formation within the resulting peptide, if a further cysteine is contained in the $[NZZ]_o$ part) or one other amino acid that is not suitable for forming a loop (giving rise to a linear peptide). The other amino acid may be the same in all cases, i.e. may be one other amino acid, or may be different, e.g. one of 3 amino acids other than cysteine. For example, when generating the randomized nucleic acid sequences, a mixture of different nucleotide triplets including one nucleotide triplets representing a codon encoding for cysteine and three nucleotide triplets each representing a codon encoding for another amino acid is used. Randomly and depending on the abundance of each nucleotide triplet in the mixture, the codon encoding cysteine or a codon encoding one of the other amino acids is integrated into the randomized nucleic acid sequence. Preferably, CorAA encodes for cysteine or one other amino acid, as this results in an even and statistically predictable coverage of corresponding linear and circular peptides in the library.

In a preferred embodiment, CorAA is a codon encoding for cysteine (C) or at least one amino acid (AA) selected from the group consisting of tyrosine, phenylalanine, asparagine, aspartic acid, glutamine, glutamic acid, histidine, lysine, isoleucine, glycine, alanine, valine, threonine, proline, leucine, serine and arginine, preferably CorAA is a codon encoding for cysteine or serine. To cover corresponding linear and circular peptides, the position CorAA within the $[NXX]_n$ [CorAA] $[NXX]_m$ part of the nucleic acid sequence is occupied by one of only two possible amino acids, namely either cysteine (allowing a loop formation within the resulting peptide) or one other amino acid that is not suitable for forming a loop (giving rise to a linear peptide). The other amino acid may be any amino acid that is not suitable for forming a loop structure. However, serine is particularly preferred as it shows similar steric properties compared to cysteine except that it cannot undergo disulfide bonding. Thus, corresponding peptides carrying a cysteine or a serine at the CorAA position are particularly similar despite that one is provided in a circular conformation.

In a preferred embodiment, each amino acid is encoded by a single codon. For most randomized libraries, the encoding nucleic acid sequence is provided by randomly adding nucleotides (adenine, thymine, cytosine, guanine) to each other to form an oligonucleotide of random sequence. This oligonucleotide is then introduced into a vector as a reading frame, such that a randomized peptide is translated from the nucleic acid sequence. Due to the redundancy of the genetic code, however, this leads to the formation of 64 different codons (each comprising three nucleotides) that represent 20 amino acids and four functional codons (start and stop codons). However, in case a start or stop codon is present within the nucleic acid sequence, it most likely encodes for a non-functional peptide. Therefore, various approaches have been developed to reduce the number of stop codons. For example, libraries were designed, in which the third position of each codon must not contain adenosine, i.e. the third nucleotide is either guanine, cytosine or thymine (so-called NNB-library), or guanine or thymine (so-called NNK-library). This eliminates the stop codons TAA and TGA and reduces the number of codons to 32 (Dennis et al., 2002). The presence of the third stop codon TAG is usually overcome by using host organisms that provide a tRNA to translate this codon into an amino acid. Nevertheless, even in libraries of the NNK or NNB type, most of the amino acids are encoded by more than one codon, such that these libraries necessarily comprise redundant peptides. Thus, for covering all possible varieties of a peptide of a given length, such a library has to provide many more encoding sequences compared to the actually expressed peptide versions. For example, to cover a randomized peptide of seven amino acids, a fully randomized library would have to cover between $32^7$ to $64^7$, i.e. $3.5 \times 10^{10}$ to $4.4 \times 10^{12}$ sequences. This is not taking into deviations from the ideal composition, which can be more than ten-fold as commonly reported for phage libraries ('t Hoen et al., 2012). Establishment and maintenance of such large libraries, however, is difficult if not impossible. For example, the number of DNA molecules that can be generated in vitro is limited and, most importantly, the efficiency of introducing the DNA into the replicating entities declines with the size of the library. Thus, using the techniques of the state of art, reliable libraries for random peptides of more than seven amino acids can hardly be generated.

In contrast, if each amino acid is encoded by a single codon, meaning all other codons encoding for the same amino acid are not used, the number of codons can be reduced to 20 exactly corresponding to the number of amino acids. This can be achieved by generating the nucleic acid sequence representing the reading frame by using oligonucleotides of three nucleotides of distinct sequence. In this case, each oligonucleotide represents one codon encoding for a distinct amino acid. The oligonucleotides are randomly combined to provide all versions of a peptide of a given length. If a single codon is used for each amino acid, the redundancy of peptides in the library is significantly reduced such that within the technical limits of the library a larger variety of peptides can be covered by a given number of sequence variants. This allows the generation of statistically more reliable libraries encoding for peptides of seven amino acids and more. For example, the diversity of a library required to cover nucleic acid sequences encoding for peptides of seven amino acids is significantly reduced compared to a usual NNK- or NNB-library, i.e. 26 fold or 460 fold, respectively. Moreover, using defined nucleotide triplets corresponding to specific codons, functional codons such as start and stop codons can be entirely excluded. This allows overcoming present limitations with respect to specific organisms that have to be used to avoid the introduction of stop codons. For example, for producing phage display libraries E. coli strains carrying suppressor tRNAs, e.g. supE or supF, are the most used organism as it translates the codon TAG into glutamine instead of recognizing the same as a stop codon (Bossi 1983).

In a preferred embodiment, at least 25 percent, preferably at least 50 percent, more preferred about 30 to 50 percent, most preferred about 50 percent of CorAA encode for cysteine. The higher the probability of a cysteine contained in the [NXX]$_n$ [CorAA] [NXX]$_m$ part, the higher is the number of peptides encoded by the library, which contain a disulfide-bond and are, thus, present in a circular conformation. For providing a library covering a linear and a circular version for each encoded peptide, about 50 percent of CorAA should encode for cysteine. The amount of CorAA encoding for cysteine can be determined, e.g. by adjusting the proportion of nucleotide triplets representing codons encoding for cysteine in the mixture of triplets used for CorAA when generating the randomized nucleic acid sequence.

In a preferred embodiment, each NXX individually represents a codon encoding for any amino acid except cysteine and methionine. Methionine contains a thioether group which is subjected to gradual oxidation leading to the formation of methionine sulfoxid and methionine sulfone. Therefore, the amount of methionine present in a library, decreases over time. Experiments with phage display libraries revealed that already after a second round of selection hardly any methionine is present in the peptides of the library. This is particularly important as the oxidation products show different binding properties compared to methionine. Therefore, a peptide of the library containing an oxidation product of methionine may show binding affinities to a given target, whereas the same peptide containing methionine would not. Thus, reducing the amount of methionine in the peptides encoded by the library is advantageous. Accordingly, in a preferred embodiment, each NZZ individually represents a codon encoding for any amino acid except methionine. More preferred, neither NXX, NZZ nor CorAA encode for methionine such that the library exclusively encodes for peptides devoid of methionine. Instead of excluding methionine, a non-natural amino acid having a similar structure and showing similar interaction properties as methionine, but lacking the thioether group, may be incorporated.

In a preferred embodiment, each NXX individually represents a codon encoding for any amino acid except cysteine and tryptophane. Including tryptophane in the peptides encoded by the library promotes unspecific binding of the peptide to a target and, thus, increases the occurrence of false positive results. Consequently, the reliability of the library decreases with the amount of tryptophane occurring in the peptides encoded by the library. Moreover, experiments showed that an increased level of tryptophane provides bacteriophages with a survival advantage as they propagate more successfully. As a result, phages expressing peptides containing few or no tryptophane, which are expected to show more reliable binding properties, are outnumbered. After several rounds of selection this leads to an enrichment of false positive results due to high levels of tryptophane, whereas the truly binding peptides are lost. Finally, tryptophane is particularly expensive to produce and chemically unstable such that for large scale production peptides devoid of tryptophane are preferred. In summary, the reduction of tryptophane in the peptides encoded by the library is advantageous for several reasons. Accordingly, in a preferred embodiment, each NZZ individually represents a codon encoding for any amino acid except tryptophane. Preferably, neither NZZ, NXX nor CorAA encode for tryptophane such that the peptides encoded by the library are devoid of tryptophane.

In a particularly preferred embodiment, each NXX individually represents a codon encoding for any amino acid except cysteine, methionine and tryptophane and each NZZ individually represent a codon encoding for any amino acid except methionine and tryptophane.

Besides methionine and tryptophane, any other amino acid may be excluded from the peptides of the library by excluding the codons encoding for the respective amino acid from the randomized nucleic acid sequence.

In a preferred embodiment, n is an integer from 2 to 20, preferably from 5 to 15.

In a preferred embodiment, m is an integer from 2 to 15, preferably from 5 to 10.

In a preferred embodiment, o is an integer from 2 to 20, preferably from 5 to 15.

In a preferred embodiment the randomized nucleic acid sequence comprises at least 21 nucleotides, preferably 21 to 120 nucleotides, more preferred 21 to 90 nucleotides, most preferred 24 to 60 nucleotides. The library of the invention is suitable for covering larger peptides than conventional libraries, because it avoids certain limitations as described above. For providing a randomized peptide of at least 7 amino acids, the nucleic acid sequences comprises 21 nucleotides in the reading frame. Using the library of the invention, however, peptides of more than 7 amino acids can be encoded. This is advantageous as larger peptides show more complex tertiary structures increasing their binding specificity to possible target molecules.

In a preferred embodiment, the library comprises at least $10^5$, preferably at least $10^7$, most preferred at least $10^9$ replicating entities. Due to the reduced diversity of the library of the invention, already the size of $10^5$ replicating entities is suitable to cover at least 50% of the number of replicating entities, which are needed to cover the variability required for a full coverage of all possible tetrameric peptides formed by the amino acids represented in all positions of the library.

In a further aspect, the invention is directed to a set of recombinant vectors, each vector comprises a randomized nucleic acid sequence, having the reading frame structure [NXX]$_n$ [CorAA] [NXX]$_m$ [NZZ]$_o$, or [NZZ]$_o$ [NXX]$_m$ [CorAA] [NXX]$_n$, wherein each NXX is independently a codon encoding for any amino acid except cysteine, CorAA is a codon encoding for cysteine or at least one other amino acid, each NZZ is independently a codon encoding for any amino acid, and n is an integer from 0 to 40, m is an integer from 1 to 20, o is an integer from 1 to 40, and at least 20 percent of CorAA encode for cysteine. The set of vectors is suitable to produce a library of replicating entities by introducing each vector into a replicating entity, e.g. a cell or a virus. The peptide encoded by the nucleic acid sequence is then produced either by the replicating entity itself (in case of a cell) or by use of a host (in case of a virus). The term "vector" as used herein refers to a DNA or RNA molecule used as a vehicle to introduce foreign genetic material in a replicating entity. The vector is replicated either by the entity itself or by use of a host. The vector may exist in the replicating entity as an individual molecule or incorporated into the entity's genome. Vectors include plasmids, viral vectors, phagemids, cosmids and artificial chromosomes.

In a preferred embodiment, the vector further comprises a regulated promoter controlling the expression of the randomized nucleic acid sequence, preferably the promoter is repressable. The activity of the promoter determines the amount of peptide produced and incorporated into the replicating entity. For example, in case of display libraries the peptide becomes localized at the surface of the replicating unit. Thus, the stronger the promoter the more peptides are presented at the surface of the replicating entity. A high amount of peptides, however, can cause an unspecific binding affinity of the replicating entity to a target molecule. As a result, the replicating entity would be enriched in selection processes due to its strong binding to the target, the peptide itself, however, would lack any specific binding properties. Thus, using a strong promoter increases the occurrence of false positive results. Therefore, it is preferred to use a regulated promoter such that the amount of peptide produced can be controlled. The regulation can for example occur via repression by compounds that can be added to the cell culture when propagating the replicating entity. Suitable promoters are e.g. those controlled by catabolics or metabolics of the replicating entity such as the Lac promoter or the PL promoter in case of bacteriophage systems. For example, using a Lac promoter, the production of peptides can be reduced by adding glucose to the bacterial culture when generating the bacteriophages. The $P_L$ promoter is even more preferred as it shows a rather low basic activity. The resulting bacteriophages carry only few peptides at their surface and thus lead to more precise and reliable screening results. A second effect of the promoter strength is an adverse counterselection. Since different peptide sequences will exhibit more or less toxic or growth limiting effects on the host, high expression usually depletes libraries of such genes coding for these peptides and generates a bias towards genes that are less harmful for the host. These clones have an advantage in replication over other sequences and significantly impair the selection.

In a preferred embodiment, the vector further comprises an endogenous gene of a replicating entity and the randomized nucleic acid sequence is located adjacent to the endogenous gene. This allows the production of a fusion protein, such that the peptide is translated as part of the endogenous protein of the replicating entity. Preferably, the nucleic acid sequence is positioned such that the peptide is fused to the N- or C-terminus of the endogenous protein. As a result, the peptide is processed and located within the replicating entity together with the endogenous protein.

In a particular preferred embodiment, the endogenous gene encodes for a surface protein of the replicating entity, preferably for a phage coat protein, more preferred for gene III of M13. Expressing the peptide as a fusion protein with a surface protein of the replicating entity results in the presentation of the peptide on the surface of the replicating entity. For example, in case the entity is a cell, the protein may be a surface receptor or a membrane protein and the peptide may be fused thereto such that it is presented at the outside surface of the cell. Displayed on the surface of the cell, the peptide can well interact with any target of interest. Similarly, in a phage display library, the randomized nucleic acid sequence is positioned next to a gene encoding for a coat protein of the phage, preferably the gene III of M13. The peptide is then generated as a fusion protein of the coat protein and localized to the head of the phage, where it is free to interact with target molecules.

In a preferred embodiment, the vector further comprises a nucleic acid linker placed between the randomized nucleic acid sequence and the endogenous gene, the linker and the endogenous gene each comprises a restriction site, and the restriction site of the endogenous gene is located in the terminal portion of the gene that is located adjacent to the linker, such that upon cleavage the randomized nucleic acid sequence is fused to an inner portion of the endogenous gene. Upon cleavage the linker and the terminal portion of the endogenous gene are deleted such that the randomized nucleic acid sequence is fused to an interior region of the gene. Accordingly, the peptide is generated as a fusion protein of the endogenous protein, however, lacking the deleted terminus. In display libraries, unspecific binding often occurs due to an interaction of the peptide with the adjacent terminus of the endogenous protein. In other words, the binding affinity observed in the screening is due to the influence of the terminus of the endogenous protein to which the peptide was fused and can not be reproduced by the peptide only. By deleting the terminal portion and fusing the randomized nucleic acid sequence to an internal portion of the endogenous gene, the specificity of the peptide-target interaction can be validated in a second round of selection. In case the replicating entity no longer interacts with the target after deletion of the terminal part of the endogenous gene, the peptide is unlikely to show specific binding properties itself and should be excluded from further examinations. In case, however, the binding affinity still persists, the peptide is likely to possess specific binding properties.

In a preferred embodiment, the vector comprises a type IIs restriction enzyme cleavage site within the randomized nucleic acid sequence and a type IIs restriction enzyme recognition site adjacent to the randomized nucleic acid sequence, wherein the cleavage site comprises a non-palindromic sequence. By cleavage and subsequent random religation, it is possible to recombine randomized nucleic acid sequences, thereby increasing the variability of the set of recombinant vectors. Preferably, the restriction site is located between the part of the nucleic acid sequence comprising $[NXX]_n$ $[CorAA]$ $[NXX]_m$ and the part of the nucleic acid sequence comprising $[NZZ]_o$. Cleavage and religation may be carried out after a first selection, increasing the variability of peptides already known to show certain binding affinities. Preferably, the restriction site is cleaved by a type IIs enzyme, which cleaves in about 15 base pairs distance from the recognition site. Thus, the recognition site can be located outside the nucleic acid sequence while the enzyme still cleaves within the reading frame. As the restriction site is non-palindromic redirected ligation is ensured. By cleaving and religating the vectors, it is possible to increase the variability of vectors from $10^4$ to $10^8$. In contrast to previously described technologies (e.g. WO9833901 (A2), the usage of libraries from codon based synthesis does not require any generation of special subsets.

In a preferred embodiment the type IIs restriction enzyme recognition site is located within a sequence insert located between a first and a second part of the randomized nucleic acid sequence. This allows cleavage at the edge of the degenerated sequence and the generation of non-palindromic overhanging sequences at the cleavage site. For example, the vector may be used to generate a first library in the display vector, which is used for a first screening.

Subsequently, the vectors are isolated from those replicating entities, which were enriched in the first screening, cleaved and recombined as described herein after removal of the linker. The particular advantage is that a primary library size of only the order of magnitude of the larger part of the randomized nucleic acid sequence allows generating a library of the maximum complexity through recombination. Since recombined DNA is more efficient in transforming the host (Collins et al., 2001), the overall work and the amount of oligonucleotides required for the cloning are significantly reduced.

In a further aspect, the invention relates to a set of randomized oligonucleotides, each oligonucleotide having the structure $[NXX]_n$ [CorAA] $[NXX]_m$ $[NZZ]_o$, or $[NZZ]_o$ $[NXX]_m$ [CorAA] $[NXX]_n$ wherein each NXX is independently a codon encoding for any amino acid except cysteine, CorAA is a codon encoding for cysteine or at least one other amino acid, each NZZ is independently a codon encoding for any amino acid, and n is an integer from 0 to 40, m is an integer from 1 to 20, o is an integer from 1 to 40, and at least 20 percent of CorAA encode for cysteine. This set of oligonucleotides is suitable for producing the vectors and the library of the invention. The oligonucleotides encode for randomized peptides when introduced into the reading frame of a vector.

In a preferred embodiment, each codon encodes for a different amino acid. Thereby, a reduction to about 20 codons, corresponding to the number of amino acids, is possible. The number of codons can be reduced by using triplets of nucleotides corresponding to distinct codons, for generating the oligonucleotides. Each triplet of nucleotides corresponds to one codon representing one amino acid. For generating the oligonucleotides the triplets are randomly assembled. For example, when synthesizing the oligonucleotide, a mixture of nucleotide triplets each representing a codon of an amino acid, wherein each amino acid is represented once, is used for each NZZ position. Alternatively, the randomized oligonucleotides may be generated using Slonomics technology (Van den Brulle 2008). Additionally, for NXX positions a similar mixture of nucleotide triplets is used, however, lacking the nucleotide triplet representing the codon for cysteine. For the position CorAA a mixture of at least two different nucleotide triplets is used of which one encodes for cysteine and the other encodes for one other amino acid, preferably serine. As a result, at the position CorAA either cysteine or one other amino acid is located, whereas all other positions may encode for any amino acid, except of cysteine in the case of NXX. Moreover, the frequency with which the individual amino acids occur in the peptides, may be varied by adjusting the proportion of each nucleotide triplet contained in the mixture used for generating the oligonucleotide. In particular, the proportion of triplets representing codons for cysteine in the mixture for CorAA influence the abundance of circular peptides versus linear peptides. Furthermore, the proportion of triplets corresponding to codons of methionine, tryptophane and/or any other amino acid may be reduced in comparison to triplets encoding for other amino acids. Consequently, only few of the peptides encoded by the library will comprise a methionine and/or tryptophane.

In a preferred embodiment, each NXX and NZZ individually is one codon selected from each group, namely group 1 consisting of GCT, GCC, GCA, and GCG, group 2 consisting of TTA, TTG, CU, CTC, CTA, and CTG, group 3 consisting of CGT, CGC, CGA, CGG, AGA, and AGG, group 4 consisting of AAA and AAG, group 5 consisting of AAT and AAC, group 6 consisting of ATG, group 7 consisting of GAT and GAC, group 8 consisting of TTT and TTC, group 9 consisting of CCT, CCC, CCA and CCG, group 10 consisting of CAA and CAG, group 11 consisting of TCT, TCC, TCA, TCG, AGT and AGC, group 12 consisting of GAA and GAG, group 13 consisting of ACT, ACC, ACA and ACG, group 14 consisting of GGT, GGC, GGA and GGG, group 15 consisting of TGG, group 16 consisting of CAT and CAC, group 17 consisting of TAT and TAC, group 18 consisting of ATT, ATC and ATA, group 19 consisting of GU, GTC, GTA and GTG and group 20 consisting of TGT and TGC. As NXX may not encode for cysteine, group 20 only applies to NZZ. Furthermore, the codons used to encode for a specific amino acid may differ for NXX and NZZ. To increase the variability of the library, the number of codons is reduced, preferably to the number of amino acids represented in the peptides encoded by the library, in generally 20. To do so, each amino acid is represented by a single codon, such that during oligonucleotide synthesis no more than 20 different nucleotide triplets each representing a codon of a different amino acid, are used. Accordingly, from each group of codons encoding for the same amino acid, for example group 1 encoding for alanine, only one is selected and used. Thus, from each of the groups of codons listed in table 1, one codon is selected and a corresponding nucleotide triplet is used for generating the randomized oligonucleotides of the invention.

In a preferred embodiment, each NXX and NZZ individually is one codon selected from each group, namely group 1 consisting of GCT, GCC, GCA, and GCG, group 2 consisting of TTA, TTG, CU, CTC, CTA, and CTG, group 3 consisting of CGT, CGC, CGA, CGG, AGA, and AGG, group 4 consisting of AAA and AAG, group 5 consisting of AAT and AAC, group 7 consisting of GAT and GAC, group 8 consisting of TTT and TTC, group 9 consisting of CCT, CCC, CCA and CCG, group 10 consisting of CAA and CAG, group 11 consisting of TCT, TCC, TCA, TCG, AGT and AGC, group 12 consisting of GAA and GAG, group 13 consisting of ACT, ACC, ACA and ACG, group 14 consisting of GGT, GGC, GGA and GGG, group 16 consisting of CAT and CAC, group 17 consisting of TAT and TAC, group 18 consisting of ATT, ATC and ATA, group 19 consisting of GTT, GTC, GTA and GTG and group 20 consisting of TGT and TGC. In this case the peptides encoded by the library are devoid of methionine and tryptophane.

In a preferred embodiment, each NXX individually is selected from the group consisting of AAA, AAT, ACT, ATA, CAG, CAT, CCA, CGT, CTG, GAA, GAC, GCC, GGT, GTT, TAC, TCT, TGG, TTT, and each NZZ individually is selected from the group consisting of AAA, AAC, ACT, ATC, CAG, CAT, CCA, CGT, CTG, GM, GAC, GCT, GGT, GTT, TAC, TCT, TGC, TTC. Within one cell, not all codons are incorporated during translation with the same frequency. This is because tRNAs for some codons are less abundant than others. This can cause peptides having amino acids encoded by less frequent codons to be underrepresented in the library as fewer proteins are translated from such nucleic acid sequences. In the unfortunate event that the corresponding tRNA is entirely absent, translation of the peptide would be terminated prematurely, such that no peptide or a truncated peptide would be produced. Both reduces the reliability of a library. To avoid these problems, codons are selected, which are equally well processed and translated leading to a reliable distribution of amino acids within the peptides encoded by the oligonucleotides.

In a preferred embodiment, the oligonucleotide comprises at least 21 nucleotides, preferably 21 to 120 nucleotides, more preferred 21 to 90 nucleotides, most preferred 24 to 60 nucleotides.

In a preferred embodiment, the set of randomized oligonucleotides comprises at least $10^5$, preferably at least $10^7$, most preferred at least $10^9$ different oligonucleotides.

In a further aspect, the invention relates to a method for generating a library of replicating entities comprising the steps providing a set of randomized oligonucleotides of the invention, introducing each oligonucleotide into a replicating entity, and propagating the replicating entities as individual clones. The introduction of the oligonucleotides into the replicating entities may be, for example, achieved by incorporating each oligonucleotide into a vector such that the peptide is translated from the vector when introduced into a cell. For introducing the vector into the replicating entity various techniques depending on the kind of entity used are available. In case of a cell, e.g. a yeast cell, chemical or electrical transformation may be employed for introducing the vector into the cell. Alternatively, the vector may be transferred into a cell by transfection, e.g. using a virus particle as a carrier. After introduction, the vector may be maintained in the cell as an individual nucleic acid molecule, e.g. a plasmid, or integrated into the endogenous DNA or RNA. In case the replicating entity is a virus, e.g. a bacteriophage, the vector is introduced into a host cell, e.g. E. coli, which then produces the virus, or bacteriophage. In case of eukaryotic cells, sophisticated virus packaging cell lines are available. Finally, the replicating entities are propagated as clones, in case of bacteriophages by use of a host cell, such that each clone expresses one of the randomized peptides encoded by the library.

In a preferred embodiment, introducing the oligonucleotide into the replicating entity comprises incorporating the oligonucleotide into a recombinant vector comprising an endogenous gene of the replicating entity such that the oligonucleotide is located adjacent to the endogenous gene. The oligonucleotide is incorporated into the vector directly following a gene encoding for an endogenous protein of the replicating entity. This allows the expression of the randomized peptide as a fusion protein together with the endogenous protein of the replicating entity. Moreover, if the randomized peptide encoded by the oligonucleotide is expressed as a fusion protein together with a surface molecule, it is integrated into the viral envelope or phage head, respectively. Preferably, the vector is a phagemid.

In a preferred embodiment, the method further comprises the steps introducing each oligonucleotide into a recombinant vector, cleaving the recombinant vectors within the oligonucleotide, randomly ligating the vectors to form a concatamere, cleaving the recombinant vectors outside the oligonucleotide, and religating the vectors to generate novel circular recombinant vectors. By cleaving and randomly religating the vector, it is possible to significantly increase the variety of the library. Cleavage may be done after a first round of selection thereby specifically increasing the variability of peptides already showing certain binding affinity to the target. In detail, the oligonucleotides are designed as to include a cleavage site, preferably a cleavage site for a type IIs restriction enzyme, e.g. as described herein. To ensure correct ligation, the cleavage site is designed such that upon cleavage non-palindromic termini are generated. The oligonucleotide is then integrated into a vector, e.g. a plasmid or phagemid, which is introduced into a cell, e.g. to produce bacteriophages. The replicating entities carrying the oligonucleotide are then subjected to a first round of selection to identify potential binding partners of the target molecule. In case of a phage display, the bacteriophages are brought into contact with the target and selected for those binding to the target. Subsequently, the vectors are extracted from the replicating entities that were found to interact with the target and digested with a restriction enzyme cleaving the recombinant vectors within the oligonucleotide. Ligation of the linearized vectors leads to the formation of a concatamere of multiple vectors. These concatameres are then cleaved with a restriction enzyme recognizing a restriction site located outside the oligonucleotide leaving linearized vectors, which are religated to form novel circular recombinant vectors. These vectors are then reintroduced in cells, e.g. to produce new bacteriophages. Interestingly, cleavage and religation of the vectors does not only increase the variety of the randomized peptides but the religated vectors were found to transform with much higher efficiency compared to the original vectors.

In a preferred embodiment, the method further comprises the steps including a nucleic acid insert into each oligonucleotide, introducing each oligonucleotide into a recombinant vector, cleaving the recombinant vectors to excise the insert, randomly ligating the vectors to form a concatamere, cleaving the recombinant vectors outside the oligonucleotide, and religating the vectors to generate novel circular recombinant vectors. Instead of designing the oligonucleotide such as to include a restriction site, the oligonucleotide may include an insert located between a first and a second part of the randomized nucleic acid sequence, which comprises the restriction site. Preferably the restriction site is a type IIs restriction site.

In a further aspect, the invention relates to a method for identifying an amino acid polymer able to interact with a target, comprising the steps providing a library of replicating entities of the invention, bringing the library into contact with the target, and enriching the replicating entities interacting with the target. The library of the invention is particularly suitable for screening for interaction partners of a given target. The term "target" as used herein refers to any kind of molecule, preferably to a biomolecule, e.g. a peptide, protein or chemical compound. For example, using the present method, amino acid polymers acting as agonists or antagonists to a target receptor can be identified. Likewise, diagnostic tools for detecting a given target compound can be established based on the interaction of the amino acid polymer and the target compound. The library provides a large variety of randomized amino acid polymers (also referred to as peptides), as linear and circular versions. The peptides may be presented on the surface of the replicating entities, each entity presenting an individual amino acid polymer. Further, each peptide may be presented as such or as part of a larger molecule, e.g. a protein. The peptides are brought into contact with the target molecule by means of the replicating entities in a single screening. For example, the target molecule may be immobilized on a surface, to which the library e.g. the bacteriophages in case of a phage display library, are added. Subsequently, those replicating entities carrying a peptide, which is able to interact with the target are enriched, e.g. by a washing step removing non- and weak-binding replicating entities. The remaining bound entities may then be eluted and collected.

In a preferred embodiment, the method further comprises the steps sequencing the genetic material of the enriched replicating entities and determining an interaction between the amino acid polymer encoded by the replicating entities and the target. By sequencing the genetic material of the replicating entity, the randomized nucleic acid sequence is identified, which encodes for the amino acid polymer. Preferably, sequencing is performed using Next-Generation-Sequencing techniques (Metzker, 2005). After determining the nucleic acid sequence, the amino acid polymer is produced, e.g. by solid phase synthesis and its ability to interact with the target is verified. For example, the interaction between the amino acid polymer and the target may be determined by using a chemical reaction or a physical signal depending on the binding of the amino acid polymer to the target.

EXAMPLES

Material

Vent Proof-reading polymerase was provided from New-England Biolabs and dNTPs from Life Technologies. PCR-Oligos were provided from Eurofins Genomics. Point-mutations were performed with the QuickChange site-Directed Mutagenesis kit (Agilent). Restriction enzymes were provided either from Thermo Scientific or New England Biolabs. PCR-products were purified with the QIAquick PCR purification kit (Qiagen). Vector-DNA was purified using the Gel extraction kit (Omega, bio-tek). PCR-fragments were purified with the Nucleotide removal kit (Qiagen). DNA-ligations were carried out with T4 ligase (Thermo Scientific). TOP10F' cells were supplied from Life Technologies and the phage lambda lysogen TG1(λ) was generated from *E. coli* K12 TG1 (originally obtained from D. Legendre, Université Catholique de Louvain, Belgium) after infection with lambda phage.

Methods

Plasmid DNA containing the gene 3 driven by the pL-promoter was transformed in TG1(λ) whereas plasmid DNA containing the gene 3 controlled by the LacI-promoter was transformed in TOP10F'. KS(+) and derived KS(+)K DNA was transformed in TOP10F'. Both vectors used for the ENTE1 and ENTE2 libraries were constructed in several steps. PCR conditions and primers are described in the tables.

Construction of pPepPr3A-Stuffer (ENTE1)

All vectors were derived from the pMAMPF vector (GenBank: M33637.1).

pPepPr1-mut1: creation of a BglII restriction site with the QuickChange site-Directed Mutagenesis kit (see table 2).

pPepPr1-mut2: creation of a second BglII restriction site with the QuickChange site-Directed Mutagenesis kit (see table 2).

pPepPr1-mut3: elimination of the Chloramphenicol acetyltransferase gene. pPepPr1-mut2 was digested with the restriction enzyme BglII. Digested pPepPr1-mut2 was gel purified and self-ligated.

pPepPr1-mut2: elimination of one BpmI restriction site with the QuickChange site-Directed Mutagenesis kit (see table 2).

pPepPr2: elimination of a second BpmI restriction site with the QuickChange site-Directed Mutagenesis kit (see table 2).

pPepPr2-mut1: elimination of the BsmBI restriction site with the QuickChange site-Directed Mutagenesis kit (see table 2).

pPepPr2-mut2: elimination of the BsaI restriction site with the QuickChange site-Directed Mutagenesis kit (see table 2).

pPepPr3: elimination of the EarI restriction site with the QuickChange site-Directed Mutagenesis kit (see table 2).

pPepPr3-stuffer: cloning of β-galactosidase gene between the NaeI and BstXI restriction sites of pPepPr3. The gene was amplified through PCR (see table 1). The vector and β-galactosidase gene were digested with NaeI and BstXI, purified and ligated.

pPepPr3-stuffer-mut2: creation of a BsgI restriction site in the leader sequence with the QuickChange site-Directed Mutagenesis kit (see table 2).

pPepPr3A-stuffer (FIG. 1A, SEQ ID NO.: 44): cloning again of the β-galactosidase gene between the NaeI and BstXI restriction sites of pPepPr3. In addition, the primers were designed to create two BsmBI sites. The β-galactosidase gene was amplified through PCR. The vector and gene were digested with NaeI and BstXI, purified and ligated.

Construction of pPEPPR7B-Stuffer (ENTE2)

The pL-promoter of pPepPr3A-stuffer was replaced by the LacI-promoter. 3 BstXI, one BsmBI and one KpnI restriction sites were mutated. Two vectors, pFAB74 and KS(+) were used for subcloning. LacI comes from pFAB74. Three BstXI restriction sites of LacI were mutated in pFAB74. Then, LacI was cloned in KS(+) and 1 BsmBI and one KpnI restriction sites were mutated.

pFAB74mut5: elimination of one BstXI restriction site with the QuickChange site-Directed Mutagenesis kit (see table 2). pFAB74 contains the LacI promoter.

pFAB74mut54: elimination of one BstXI restriction site with the QuickChange site-Directed Mutagenesis kit (see table 2).

pFAB74mut543: elimination of one BstXI restriction site with the QuickChange site-Directed Mutagenesis kit (see table 2).

KS(+)K: the KpnI restriction site was removed after digestion with KpnI and digestion with Klenow.

KS(+)KLacI: the LacI-promoter was amplified through PCR (see table 2). KS(+)K and LacI were digested with XbaI and EcoRI, purified and ligated.

KS(+)KLacI189: KS(+)KLacI was modified to remove one BsmBI restriction site in the LacI-promoter. A 205-bp fragment was amplified by PCR (see table 2). One primer containing the KasI restriction site was designed to introduce a mutation in the BsmBI restriction site close to KasI. KS(+)K and the purified PCR-fragment were digested with HpaI and KasI, purified and ligated.

KS(+)KLacI189255: KS(+)KLacI189 was modified to remove one KpnI restriction site in the LacI-promoter. A 261-bp fragment was amplified by PCR (see table 2). Primers were designed to contain a KasI restriction site and a BstXI restriction site. KpnI is compatible with BstXI therefore KpnI and BstXI disappear after ligation. KS(+) KLacI189 was digested with KasI and KpnI, and the purified PCR-fragment was digested with KasI and BstXI. Then, the vector and the insert were purified and ligated.

pPepPr5A-stuffer: the BsgI restriction site was removed. The promoter/leader sequence was recovered from pPepPr2 through PCR, digestion with BglII and NaeI and cloned between the same restriction sites of pPepPr3A-stuffer. pPepPr2 does not have the restriction site BsgI upstream of NaeI.

pPepPr6A-stuffer: insertion of one BglII restriction site in the 5'UTR of gene3 with the QuickChange site-Directed Mutagenesis (see table 2).

pPepPr7Ac2-stuffer: insertion of the LacI between the two BglII restriction sites. LacI was amplified through PCR (see table 2). pPepPr6a-stuffer and LacI were digested with BglII, purified and ligated.

pPepPr7A-stuffer: truncation of a region upstream of LacI. A 1000-bp fragment was amplified through PCR (see table 2). pPepPr7Ac2-stuffer and PCR product were digested with BstBI and EcoRV, purified and ligated. It leads also to the elimination of one BglII restriction site upstream of LacI.

pPepPr7B-stuffer (FIG. 1B, SEQ ID NO.: 45): reparation of the OmpA region. A 499-bp fragment was amplified through PCR (see table 2). pPepPr7A-stuffer and PCR product were digested with EcoRV and NruI, purified and ligated. It results also of the elimination of the second BglII restriction site downstream of LacI.

TABLE 2

PCR conditions for construction of pPepPr3A-stuffer and pPEPPR7B-stuffer

| PCR purpose/ construction | template | Primer sets | comments |
|---|---|---|---|
| pPepPr1-mut1 | pPepPr1 | BglII-mut-F1 and BglII-mut-R1 | Creation of one BglII restriction site |
| pPepPr1-mut2 | pPepPr1-mut2 | BglII-mut-F2 and BglII-mut-R2 | Creation of a second BglII restriction site |
| pPepPr2 | pPepPr1-mut3 | BpmI-mut-F and BpmI-mut-R | Elimination of one BpmI restriction site in the beta-lactamase gene |
| pPepPr2-mut1 | pPepPr2 | BsmBI-mut-F1 and BsmBI-mut-R1 | Elimination of one BsmBI restriction site. Creation of one XhoI site |
| pPepPr2-mut2 | pPepPr2-mut1 | BsaI-mut-F1 and BsaI-mut-R1 | Elimination of one BsaI restriction site |
| pPepPr3 | pPepPr2-mut2 | EarI-mut-F1 and EarI-mut-R1 | Elimination of one EarI restriction site |
| β-galactosidase | puc19 | stuffer-BstXI-F and stuffer-NaeI-R | Amplification of a beta-galactosidase gene for cloning in pPepPr3 |
| pPepPr3-stuffer-mut2 | pPepPr3-stuffer | BsgI-mut-F1 and BsgI-mut-R1 | Creation of one BsgI restriction site in the leader sequence |
| β-galactosidase | puc19 | BsmBI-mut-F2 and BsmBI-mut-R3 | Amplification of a beta-galactosidase gene gene for cloning in pPepPr3-stuffer-mut2 |
| pFAB74mut5 | pFAB74 | Lac-BstXIm5-F and Lac-BstXIm5-R | Elimination of one BstXI restriction site |
| pFAB74mut54 | pFAB74mut5 | Lac-BstXIm4-F and Lac-BstXIm4-R | Elimination of one BstXI restriction site |
| pFAB74mut543 | pFAB74mut54 | Lac-BstXIm3-F and Lac-BstXIm3-R | Elimination of one BstXI restriction site |
| LacI | pFAB74mut543 | Lac-F1 and Lac-R1 | Amplification of LacI for cloning in KS(+)K |
| 205-bp | pFAB74mut543 | LacI-EcoRV-F and LacI-KasI-R | Amplification of a fragment of LacI for cloning in KS(+)K |
| 261-bp | pFAB74mut543 | LacI-F2 and LacI-BstXI-R | Amplification of a fragment of LacI for cloning in KS(+)K |
| pPepPr6A-stuffer | pPepPr5A-stuffer | BglII-mut-F3 and BglII-mut-R3 | Creation of one BglII restriction site |
| pPepPr7Ac2-stuffer | KS(+)KLacI189255 | Lac-F1 and Lac-R1 | LacI amplification for cloning in pPepPr6A-stuffer |
| pPepPr7A-stuffer pPepPr7B-stuffer | pFAB74mut543 pPepPr7A-stuffer | Lac-F3 and Lac-R3 LacI-EcoRV-F and SD_OmpA-R2 | |
| ENTE1 | ENTE1 oligo | fwd1 and rev2 | Ente1 oligo amplification for cloning in pPepPr3A-stuffer |
| ENTE2 | ENTE2 oligo | Ente2-F and Ente2-R | Ente2 oligo amplification for cloning in pPepPr7B-stuffer |

TABLE 3

Primer sequences

| Name | Sequence | SEQ ID NO. |
|---|---|---|
| BglII-mut-F1 | GGCGGGCTCGAAGATCTGCCATTCATCCG | 01 |
| BglII-mut-R1 | CGGATGAATGGCAGATCTTCGAGCCCGCC | 02 |
| BglII-mut-F2 | GATCTTCCGTCACAGATCTTTATTCGAAGACG | 03 |
| BglII-mut-R2 | CGTCTTCGAATAAAGATCTGTGACGGAAGATC | 04 |
| BpmI-mut-F | CCACGCTCACCGGCACCAGATTTATCAGC | 05 |
| BpmI-mut-R | GCTGATAAATCTGGTGCCGGTGAGCGTGG | 06 |
| BsmBI-mut-F1 | CATGCAGCTCCTCGAGTCGGTCACAGCTTGTC | 07 |

TABLE 3-continued

Primer sequences

| Name | Sequence | SEQ ID NO. |
|---|---|---|
| BsmBI-mut-R1 | GACAAGCTGTGACCGACTCGAGGAGCTGCATG | 08 |
| BsaI-mut-F1 | GCTGCAATGATACCGCGCGACCCACGCTCAC | 09 |
| BsaI-mut-R1 | GTGAGCGTGGGTCGCGCGGTATCATTGCAGC | 10 |
| EarI-mut-F1 | GCTTCAATAATATTGAAAAGGATGAGTATGAGTATTCAACATTTCC | 11 |
| EarI-mut-R1 | GGAAATGTTGAATACTCATACTCATCCTTTTCAATATTATTGAAGC | 12 |
| Stuffer-BstX1-F | AATTTCCACACCACTGGTGAGTGAGCTGATACCGC | 13 |
| Stuffer-NaeI-R | AATTTGCCGGCTCGCGCGTTTCGGTGATG | 14 |
| BsgI-mut-F1 | GTTTCGCTACCGTAGTGCAGGCCGGCGATAATG | 15 |
| BsgI-mut-R1 | CATTATCGCCGGCCTGCACTACGGTAGCGAAAC | 16 |
| Lac-BstXIm5-F | CGATCAACTGGGTGCGAGCGTGGTGGTGTCG | 17 |
| Lac-BstXIm5-R | CGACACCACCACGCTCGCACCCAGTTGATCG | 18 |
| Lac-BstXIm4-F | GCTGAATTACATTCCGAACCGCGTGGCACAAC | 19 |
| Lac-BstXIm4-R | GTTGTGCCACGCGGTTCGGAATGTAATTCAGC | 20 |
| Lac-BstXIm3-F | GGATGCCATTGCTGTCGAAGCTGCGTGCACTAATGTTCCG | 21 |
| Lac-BstXIm3-R | CGGAACATTAGTGCACGCAGCTTCGACAGCAATGGCATCC | 22 |
| LacI-F1 | ATTTCTAGATCTACCGTATTACCGCCTTTGAG | 23 |
| LacI-R1 | AATTTGAATTCAGCTGTTTCCTGTGTGAAATTG | 24 |
| Lac-EcoRV-F | TGCGGATATCTCGGTAGTGG | 25 |
| Lac-KasI-R | ATTGGGCGCCAGGGTGGTTTTTCTTTTCACCAGTGACACGGGCAACAGCTG | 26 |
| Lac-BstXI-R | AATTCCAGGTACATGGAGCTCACTGCCCGCTTTCC | 27 |
| BgIII-mut-F3 | CCAAGGAGGTCTAGATAACGAGGGAGATCTATGAAAAGACAGCTATCGC | 28 |
| BgIII-mut-R3 | GCGATAGCTGTCTTTTCATAGATCTCCCTCGTTATCTAGACCTCCTTGG | 29 |
| LacI-F3 | TTAATTCGAAACCGTATTACCGCCTTTGAG | 30 |
| LacI-R3 | TTAAGATATCCGCACCAACGCGC | 31 |
| SD_OmpA-R2 | TTTAATCGCGATAGCTGTCTTTTCATTTTTTGCCCTCGTGTGAAATTGTTATCCGC | 32 |
| fwd1 | GTGTCGACGTCTCCCGGC | 33 |
| rev2 | ACGTCTCCCTCCGCTGGAG | 34 |
| Ente2-F | GTGTCGACGTCTCCCGGC | 35 |
| Ente2-R | CTGTCGACGTCTCCCTCC | 36 |

Construction ENTE-1 Library

For generating the ENTE-1 library (FIG. 2) dsDNA oligo sequences having the structure (SEQ ID NO.: 37)
GTGTCGACGTCTCCCGGCN##N##N++TSCN##N##N##N##NZZNZZNYYNZZNZZNZZNZZNNCTCCAGCGGAGGGAGACGTCGACAG and (SEQ ID NO.: 38)
CACAGCTGCAGAGGGCCGN##N##N++ASGN##N##N##N##NZZNZZNYYNZZNZZNZZNZZNNGTGGTCGCCTCCCTCTGCAGCTGTC were generated using the mixtures of trinucleotides as listed in table 4

TABLE 4

| Encoded amino acid | Codon | NYY Inverse 3 | NZZ Mix-All (without Met and Trp) | N## Mix-All (without Cys and Met) |
|---|---|---|---|---|
| Lys | AAA | x | X | X |
| Asn | AAC | | X | |
| Asn | AAT* | | | X |
| Thr | ACT | | X | X |
| Ile | ATA* | | | X |
| Ile | ATC | x | X | |
| Met | ATG | | | |
| Gln | CAG | x | X | X |
| His | CAT* | | X | X |
| Pro | CCA | x | X | X |
| Pro | CCG* | | | |
| Arg | CGT | x | X | X |
| Leu | CTG | | x | x |
| Glu | GAA | x | X | X |
| Asp | GAC | | X | X |
| Ala | GCC | | | X |
| Ala | GCT | | X | |
| Gly | GGT | x | X | X |
| Val | GTT | | X | X |
| Tyr | TAC | x | X | X |
| Ser | TCT | | X | X |
| Cys | TGC | x | X | |
| Trp | TGG | x | | X |
| Phe | TTC | | X | |
| Phe | TTT | | | X |
| Codons used | | 10 | 18 | 18 |

*Palindrome

Sequences were amplified through PCR using the fwd1 and rev2 primers (see table 3). PCR conditions were 5 min 95° C., 5 cycles (1 min 95° C.; 1 min 58° C., 20 sec 72° C.).

For 50 µl, 10 mM dNTPs, 50 pmol each primer, 1 µl Vent polymerase (2 units), 100 ng (1.71 pmol) dsDNA oligo, 5 µl 10× vent buffer. Several PCR products were purified using the QIAquick PCR purification kit (Qiagen) according to the manufacturer's instructions. The purified product was digested with the BsmBI restriction enzyme in a concentration of 20 units/µg dsDNA for 4 hours at 37° C. Esp3I was heat inactivated at 65° C. for 20 min. DNA was ethanol precipitated overnight at −80° C. DNA was centrifuged at 22,000 g for one hour at 4° C., washed with 70% ethanol and centrifuged again at 22,000 g for 20 min at 4° C. The DNA pellet was air dried and resuspended in H$_2$O. pPepPr3A-stuffer plasmid dsDNA was digested for 4 hours at 37° C. with BsmBI restriction enzyme and SacI in a concentration of 2.5 units and 5 units/µg DNA, respectively. Vector DNA was two times gel purified using the Gel extraction kit (Omega, bio-tek). The Esp3I-digested PCR product was ligated to Esp3I-digested pPEPPR3A vector. 285 fmol vector and 1440 fmol insert were incubated with 30 units T4 ligase in 30 µl, overnight at 16° C. Ligation product was heat inactivated 10 min at 65° C. and ethanol precipitated overnight at −80° C. DNA was centrifuged at 22,000 g for one hour at 4° C., washed with 70% ethanol and centrifuged again at 22,000 g for 20 min at 4° C. The DNA pellet was air dried and resuspended in H$_2$O. 70-80 µl electrocompetent TG1(λ) in a concentration of 1.5-2.5 10$^{11}$ cells/ml were incubated with ca 60-100 ng ligation product in a 1-mm sample cuvette and pulsed by a Biorad electroporator apparatus set at 25 µF, 200Ω and 1800 V. 10-15 transformations were pooled and added to 25-30 ml pre-warmed SOC medium in a flask. Cells were shaken at 220 rpm at 37° C. for one hour and transformants were selected on dYT-plates supplemented with 200 µg/ml ampicillin. The plates were incubated at 30° C. overnight. Transformants were counted and the complexity of the library was calculated. Each plate was washed with 25-30 ml dYT to remove the bacteria. The bacteria were collected in a flask and the optical density was estimated.

To recover the phage, bacterial cells were diluted to OD 0.3 in dYT supplemented with 400 µg/ml ampicillin and cultivated one hour at 37° C. with gentle agitation. Then, M13K07 helper phage was added at MOI of 20, cells were incubated for one hour at 37° C. with gentle agitation. Then, the cells were incubated overnight at 30° C. Cells were discarded through centrifugation and phage particles present in the supernatant were precipitated with 20% PEG/2.5 M NaCl.

To prepare plasmid DNA from the cells, bacterial cells were diluted to OD 0.3 in dYT supplemented with 200 µg/ml ampicillin and cultivated overnight at 30° C. with gentle agitation. Cells were harvested and plasmid DNA was extracted and purified with the Nucleobond midiprep kit from Macherey-Nagel according the manufacturer's instructions.

Cosmix plexing was performed as follows: 50 µg DNA was digested in 50 µl with 0.35 unit BpmI/µg DNA for 4 hours at 37° C. BpmI was heat inactivated at 65° C. for 20 min. Then ca 40 µg digested DNA was ligated with 40 units T4 ligase in 50 µl for one hour at room temperature. T4 ligase was heat inactivated at 65° C. for 10 min. Then, DNA was digested in 100 µl with 0.5 units BglI/µg DNA for two hours at 37° C. BglI was heat inactivated at 65° C. for 20 min. DNA was self-ligated at a concentration of 20 ng/µl with 2.5 units/µg T4 DNA ligase, overnight at 16° C. T4 ligase was heat inactivated at 65° C. for 10 min. DNA was again digested with 1 unit BsmBI/µg DNA for 1 hour at 37° C. BsmBI was heat inactivated at 65° C. for 20 min. DNA was centrifuged at 22,000 g for one hour at 4° C., washed with 70% ethanol and centrifuged again at 22,000 g for 20 min at 4° C. The DNA pellet was air dried and resuspended in H$_2$O in a concentration of ca. 20 ng/µl.

Several transformations were performed with 20 ng DNA and 70-80 µl TG1(λ) as described above. Transformants were selected on dYT-plates containing 200 µg/ml ampicillin. Transformants were counted and the complexity of the library was calculated.

Construction of the ENTE-2 Library

The dsDNA oligo sequences GTGTCGACGTCTCCCGGCN##N##N##N##N##TST GTTGTTGCAGGCACTGCACGCCGTGCA GGCACCGTCGGTGTCTSTN##N##N##N##NZZNZZ NZZNZZNZZGGAGGG AGACGTCGACAG (SEQ ID NO.: 39) CACAGCTGCAGAGGGCCGN##N##N##N##N##AS ACAACAACGTCCGTGACGTGCGGCACGT CCGTGGCAGCCACAGASAN##N##N##N##NZZNZZ NZZNZZNZZCCTCC CTCTGCAGCTGTC (SEQ ID NO: 40) were amplified through PCR using the fwd1 and rev2 primers (Table 3). PCR conditions were 5 min 95° C., 10 cycles (1 min 95° C.; 1 min 60° C., 1 min 72° C.).

For 50 µl, 10 mM dNTPs, 50 pmol each primer, 1 µl Vent polymerase (2 units), 50 ng (1.71 pmol) dsDNA oligo, 5 µl 10× vent buffer. Several PCR products were purified using the QIAquick PCR purification kit (Qiagen) according the manufacturer's instructions. The purified product was digested with BsmBI restriction enzyme in a concentration of 40 units/µg DNA for 4 hours at 37° C. DNA was purified with the Nucleotide removal kit according the manufacturer's instructions (Qiagen). pPepPr7B-stuffer DNA was digested overnight at 37° C. with BsmBI restriction enzyme in a concentration of 1.5 unit/µg DNA. DNA was gel purified using the Gel extraction kit according the manufacturer's instructions (Omega, bio-tek). Vector DNA was again digested two hours at 37° C. with 0.8 unit BsmBI, 0.4 unit EcoRI and 0.4 unit SphI/µg DNA. Vector DNA was gel purified using the Gel extraction kit according the manufacturer's instructions (Omega, bio-tek). Linearized pPepPr7B was diluted in a concentration of 240 ng/µl. The BsmBI-digested PCR product was ligated to BsmBI-digested pPEPPR3A. 670 fmol vector and 3270 fmol insert were incubated with 30 units T4 ligase in 30 µl, overnight at 16° C. The ligation product was purified with the Nucleotide removal kit (Qiagen). 70-80 µl electrocompetent TOP10F' cells in a concentration of 1.5-2.0 10$^{11}$ cells/ml were incubated with ca 50 ng ligation product in a 1-mm sample cuvette and pulsed by a Biorad electroporator apparatus set at 25 µF, 200Ω and 2200 V. 10-15 transformations were pooled and added to 50 ml pre-warmed SOC medium in a flask. Cells were shaken at 220 rpm at 37° C. for one hour and transformants were selected on LB-plates supplemented with 200 µg/ml ampicillin and 1% glucose. The plates were incubated at 30° C. overnight. Transformants were counted and the complexity of the library was calculated.

Cosmix plexing was performed as follows: 80 µg DNA was digested in 200 µl with 0.5 unit BsgI/µg DNA, overnight at 37° C. The ligation product was purified with the Nucleotide removal kit (Qiagen). DNA was precipitated with 1 volume of 20% PEG/2.5 M NaCl for 25 min at 37° C. DNA was centrifuged at 22,000 g for 30 min at RT, washed with 70% ethanol and centrifuged again at 22,000 g for 20 min at 4° C. The DNA pellet was air dried and resuspended in H$_2$O. Then, ca 35 µg digested DNA was ligated in a concentration of 500 ng/µl with 1.4 units T4 ligase/µg DNA for 36 hours at 16° C. T4 ligase was heat inactivated at 65° C. for 10 min. Then, total DNA was digested in 100 µl with 1 unit BglI/µg DNA for three hours at 37° C. BglII was heat inactivated at 65° C. for 20 min. DNA was self-ligated in a concentration of 30 ng/μl with 2.8 units T4 DNA ligase/μg DNA, overnight at 16° C. T4 ligase was heat inactivated at 65° C. for 10 min. DNA was precipitated with 1 volume of 20% PEG/2.5 M NaCl for 15 min at 37° C. DNA was centrifuged at 22,000 g for 30 min at RT, washed with 70% ethanol and centrifuged again at 22,000 g for 20 min at 4° C. The DNA pellet was air dried and resuspended in $H_2O$. 70-80 μl TOP10F' electrocompetent cells were transformed with 130 ng DNA as described above.

Transformants were selected on LB-plates containing 200 μg/ml ampicillin and 1% glucose, counted and the complexity of the library was calculated.

Results

Quality Control of the ENTE-1 Library

Phage DNA after the final transformation of the library was sequenced by Next Generation Sequencing. The amino acid distribution deviates only in position 2 significantly from the expected similar level of all amino acids, because the leaderpeptidase ompA preferentially processes cleavage sites with certain amino acids at this $2^{nd}$ position. In all other positions the number per amino acids does not differ by more than a factor of 2 between the maximal and minimal counts. In standard libraries this value is a factor of 10 or higher (based on data from Dias-Neto et al. 2009)

Amino acid distribution in 871,069 sequences is shown in FIG. 3.

The sequence redundancy from 871069 sequences obtained in a typical run is shown in table 5. The number of sequences found more than once is particularly small. In fact, taking into account PCR artefacts, it is almost negligible.

TABLE 5

| Number of clones | Frequency |
| --- | --- |
| 854850 | 1 |
| 14873 | 2 |
| 1012 | 3 |
| 214 | 4 |
| 50 | 5 |
| 23 | 6 |
| 10 | 7 |
| 8 | 8 |
| 3 | 9 |
| 3 | 10 |
| 2 | 11 |
| 1 | 12 |
| 1 | 13 |
| 1 | 15 |
| 1 | 16 |
| 1 | 20 |
| 1 | 21 |
| 1 | 22 |
| 1 | 23 |
| 1 | 30 |
| 1 | 31 |
| 1 | 32 |
| 1 | 33 |
| 1 | 34 |
| 1 | 36 |
| 1 | 40 |
| 1 | 52 |
| 1 | 58 |
| 1 | 80 |
| 1 | 82 |
| 1 | 106 |
| 1 | 122 |

Effective Selection of Multiple Sequences

Selections were carried out on FLAG M1 and FLAG M2 monoclonal antibodies, wherein the antibodies were generated with the peptide DYKDDDDK (SEQ ID NO.: 142). The core sequence required for binding the antibody is YK plus a negative charge in the proximity or a preceding small amino acid in the case of FLAG M1.

Already after the second round, more than 95% of those sequences reliably identified by standard sequencing show a binding motif comparable with the peptide used for immunization. In contrast, comparable efforts with common phage display libraries required three rounds of selection and result in 50% or less binding clones (Srila, W. & Yamabhai, M., 2013). FLAG M1 should, according to all published literature, only recognize an N-terminal epitope and FLAG M2 any comparable epitope. However, the obtained data (table 6 and table 7) suggests that recognition of the epitope may also be possible in other positions.

TABLE 6

M1-Clones ENTE-1 Library
(FLAG-tag: DYKDDDDK (SEQ ID NO.: 142))

| | SEQ ID NO.: |
| --- | --- |
| GAHLSQRVDYKEYKVSI | 46 |
| GAHLSQRVDYKEYKVSI | 47 |
| GVLHCDYKEKIYTQSSAS | 48 |
| GNQQCRQQLVDYKYSIYS | 49 |
| GPPPCIFYADYKYNEGFS | 50 |
| GYRQSIQVDYKIRSERF | 51 |
| GYSWVSEWGFAYQVDYKIS--- | 52 |
| GHEHSWVQIDYKTAVRDS | 53 |
| GFTMSLEVDYKQKQQLF | 54 |
| GIEMSILELVDYKANLYS | 55 |
| GEAPSYQYVDYKNIVDNS | 56 |
| GEVWSYVDYKSPKKEPAS | 57 |
| GVLHCDYKFNLEYPKPNS | 58 |
| GDYRSWFVYLDYKHKLEAS | 59 |
| GYKWSEFQQSQQGALFIS | 60 |
| GYKWSEFQQSQQGALFIS | 61 |
| GYKWSEFQHFGQQGKYAS | 62 |
| GYKWSEFYKDVKQQEGAS | 63 |
| GYKWSEFVQEEKKVNKDS | 64 |
| GYKWSEFHNQFPGVQDFS | 65 |
| GYKWSETWRQVENFQHAS | 66 |
| GYKWSETTHSVQVEAHAS | 67 |
| GYKWSEIHTVFEAAQVYS | 68 |
| GYKWSELYQVERDQYFS | 69 |
| GYKWSEYLIGKPHFEHDS | 70 |
| GYKWSQYHREDKLVQEIS | 71 |

TABLE 6-continued

M1-Clones ENTE-1 Library
(FLAG-tag: DYKDDDDK (SEQ ID NO.: 142))

| | SEQ ID NO.: |
|---|---|
| GYKWSQYHREDKLVQEIS | 72 |
| GYKWSQWHDPSKEAAYDS | 73 |
| GYKWSLFHKSEEQVDEYS | 74 |
| GYKWSLWLSELKQQNEAS | 75 |
| GYKWSAINPKIQQNQDFS | 76 |
| GYKWNSFNSWSQYVPEPIS | 77 |
| GYKWNSFNSWSQYVPEPIS | 78 |
| GYKYRCLVNQVQCNEQRAS | 79 |
| GYKWQSFQHNAEQHRHPYS | 80 |
| GYKFSEILRLDYHDLVNS | 81 |
| GYKFSEILRLDYHDLVNS | 82 |
| GYKFSEIFSVYGYEPHAS | 83 |
| GYKFSEWFQISQADQPDS | 84 |
| GYKFSELQTRAYQPAVDS | 85 |
| GYKQKLYFAS | 86 |
| GYKQKLYFAS | 87 |
| GQHSVVQVGYKQKELNS | 88 |
| GYKLSELQSKTYFFPHFS | 89 |
| GAPASRGYKHKEYFVRKCS | 90 |
| GVQSSKGYKAKEQFNKAS | 91 |
| GHFHSEVSYKLKELIIYS | 92 |
| GVWVSNNWGPHQSQQTNS | 93 |

Binding motif: DYKxx(E)xx or GYKws(E)xx

TABLE 7

M2-Clones ENTE-1 Library
(FLAG-tag: DYKDDDDK (SEQ ID NO.: 142))

| | SEQ ID NO.: |
|---|---|
| GQFFSTNDSH<u>DYK</u>DEDAS | 94 |
| GPEVS<u>DYK</u>DEDPFPYFS | 95 |
| GLESRSDNFI<u>DYK</u>DLDEDS | 96 |
| GNQGSWWQ<u>DYK</u>QDDEFS | 97 |
| GPDPSNR<u>DYK</u>DWDVFSAS | 98 |
| GHQVCNYD<u>FDYK</u>DADKNS | 99 |
| GNPRSAEVYN<u>DYK</u>EQDIS | 100 |
| GEENCEHN<u>DYK</u>ECDNSYYS | 101 |
| GEENCEHN<u>DYK</u>ECDNSYYS | 102 |

TABLE 7-continued

M2-Clones ENTE-1 Library
(FLAG-tag: DYKDDDDK (SEQ ID NO.: 142))

| | SEQ ID NO.: |
|---|---|
| GEENCEHN<u>DYK</u>ECDNSYYS | 103 |
| GVFPSVIFE<u>DYK</u>ESDGDS | 104 |
| GYEQSKQP<u>DYK</u>WEDDHFS | 105 |
| GGTVCWLR<u>DYK</u>WEDEHFS | 106 |
| GGQHSEKD<u>DYK</u>WEDVRCS | 107 |
| GFNQSGF<u>DYK</u>IWDEQRIS | 108 |
| GVSGCYF<u>DYK</u>NCDETPDS | 109 |
| GHSWSEAI<u>DYK</u>WQDIRDS | 110 |
| GPFWSTWVAVH<u>DYK</u>YEDS- | 111 |
| GNRQCYL<u>DYK</u>YEDHNAAS | 112 |
| GDDWSNYLD<u>DYK</u>LEDRYS | 113 |
| GGSQSHHEA<u>DYK</u>LEDTYS | 114 |
| GGNTSWYEH<u>DYK</u>FEDQAS | 115 |
| GHQNSQWAW<u>DYK</u>HEDTFS | 116 |
| GFVVSPY<u>DYK</u>SEDTACFS | 117 |
| GANQSTDAYV<u>DYK</u>LLDYS | 118 |
| GANQSTDAYV<u>DYK</u>LLDYS | 119 |
| GHWQSAFDP<u>DYK</u>LTDTAS | 120 |
| GTVWSDGWSV<u>DYK</u>LADYS | 121 |
| GNIHS<u>DYK</u>LYDGTHATDS | 122 |
| GSLHSIWHQE<u>DYK</u>LQDFS | 123 |
| GDGWSKYFE<u>DYK</u>NCDTYS | 124 |
| GEVSSIQHW<u>DYK</u>NYDPNS | 125 |
| GPSTSWNSD<u>DYK</u>FGDVDS | 126 |
| GLPVCGEELGI<u>DYK</u>FYDS- | 127 |
| GQSTCDDPW<u>DYK</u>CCDGNS | 128 |
| GFLASKWGHFEK<u>DYK</u>CYDS- | 129 |
| GHVLSDDFV<u>DYK</u>QPDLYS | 130 |
| GSLAC<u>DYK</u>QYDPEVVRNS | 131 |
| GELHCFGENH<u>DYK</u>SADIS | 132 |
| GGRVCSYQD<u>DYK</u>SCEYS | 133 |
| GITLCAFHDYRWDDIQAS | 134 |
| GQFSSDYQIS<u>DYK</u>ELDYS | 135 |
| GKPHS<u>DYV</u>YN<u>DCK</u>QEDIS | 136 |
| GSPPCGWEAIQ<u>EYK</u>LCDS- | 137 |
| GNQGC<u>YKL</u>WP<u>E</u>CYSVYNS | 138 |
| GAGYGC<u>YLF</u>Y<u>E</u>IWYFGCCS | 139 |

TABLE 7-continued

M2-Clones ENTE-1 Library
(FLAG-tag: DYKDDDDK (SEQ ID NO.: 142))

| | SEQ ID NO.: |
|---|---|
| GVPPCNSE<u>DKY</u>CIDQFAS | 140 |
| GQYTCAWQWLLYQLCIFS | 141 |

Binding motif: <u>DYK</u>xxDxx

Fingerprinting Antibody Epitopes

Figure 4:
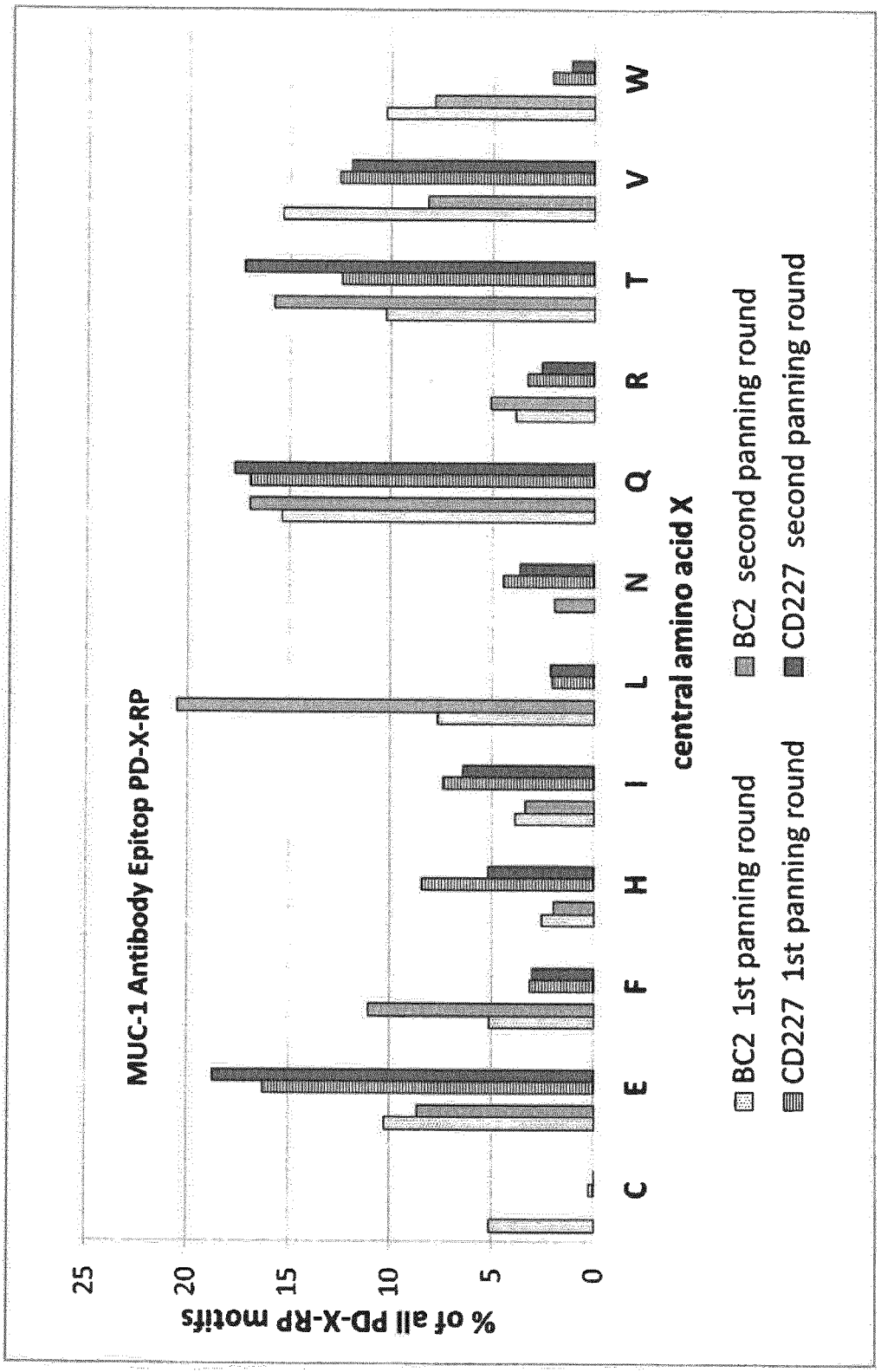
FIG. 4 shows a binding pattern analysis of the CD227 antibody and the BC2 antibody using the ENTE-1 library.

Monoclonal Antibodies CD227 (Becton, Dickinson and Company, BD Pharmingen™ Cat. No. 550486) and BC2 (PrimaBiomed USA Inc.) recognize the same site in the MUC-1 antigen PDXRP, with X being not preferred based on internal investigations applying peptide phage display and identifying less than 20 binding peptides per antibody. ENTE-1 library was used for two panning rounds on both antibodies. >200,000 sequences were determined from the first and second selection round and all patterns matching PDXRP were analyzed. The results (FIG. 4) show a clearly differentiated binding pattern with respect to negatively charged glutamic acid (E) and hydrophobic amino acids like leucine (L), suggesting that the antibodies are not identical.

REFERENCES

WO9833901 (A2)

Bossi, L. Context effects: translation of UAG codon by suppressor tRNA is affected by the sequence following UAG in the message. J. Mol. Biol. 1983; 164, 73-87.

Collins J, Horn N, Wadenbäck J, Szardenings M. Cosmixplexing: a novel recombinatorial approach for evolutionary selection from combinatorial libraries. J Biotechnol. 2001 June; 74(4):317-38.

Dennis M S, et al. Albumin binding as a general strategy for improving the pharmacokinetics of proteins. J Biol Chem 2002; 277:35035-35043.

Dias-Neto E, Nunes D N, Giordano R J, Sun J, Botz G H, Yang K, Setubal J C, Pasqualini R, Arap W. Next-generation phage display: integrating and comparing available molecular tools to enable cost-effective high-throughput analysis. PLoS One. 2009 Dec. 17; 4(12):e8338.

Metzker M L. Emerging technologies in DNA sequencing. Genome Res. 2005 December; 15(12):1767-76.

't Hoen P A, Jirka S M, Ten Broeke B R, Schultes E A, Aguilera B, Pang K H, Heemskerk H, Aartsma-Rus A, van Ommen G J, den Dunnen J T. Phage display screening without repetitious selection rounds. Anal Biochem. 2012 Feb. 15; 421(2):622-31.

Srila W, Yamabhai M. Identification of amino acid residues responsible for the binding to anti-FLAG™ M2 antibody using a phage display combinatorial peptide library. Appl Biochem Biotechnol. 2013 October; 171(3):583-9.

Van den Brulle et al. A novel solid phase technology for high-throughput gene synthesis. Biotechniques 2008; 45(3):340-3.

The invention claimed is:

1. A library of replicating entities, each entity comprises a recombinant vector comprising a randomized nucleic acid sequence, having the reading frame structure

[NXX]n [CorAA] [NXX]m [NZZ]o, or

[NZZ]o [NXX]m [CorAA] [NXX]n wherein each NXX is independently a randomized codon encoding for any amino acid except cysteine, CorAA is a codon encoding for cysteine or at least one other amino acid, each NZZ is independently a randomized codon encoding for any amino acid, and n is an integer from 0 to 40, m is an integer from 1 to 20, o is an integer from 1 to 40, and wherein a population of at least 20 percent of the replicating entities comprise a recombinant vector comprising a randomized nucleic acid sequence in which CorAA is a codon encoding for cysteine and a subset of said population has a codon encoding an amino acid other than histidine that immediately precedes the CorAA codon.

2. The library of claim 1, wherein the replicating entity is a cell or a virus.

3. The library of claim 1, wherein CorAA is a codon encoding for cysteine or at least one amino acid selected from the group consisting of Tyr, Phe, Asn, Asp, Gln, Glu, His, Lys, Ile, Gly, Ala, Val, Thr, Pro, Leu, Ser, and Arg.

4. The library of claim 1, wherein each amino acid is encoded by a single codon.

5. The library of claim 1, wherein the library is a phage display library.

6. A set of recombinant vectors, each vector comprises a randomized nucleic acid sequence, having the reading frame structure

[NXX]n [CorAA] [NXX]m [NZZ]o, or

[NZZ]o [NXX]m [CorAA] [NXX]n wherein each NXX is independently a randomized codon encoding for any amino acid except cysteine, CorAA is a codon encoding for cysteine or at least one other amino acid, each NZZ is independently a randomized codon encoding for any amino acid, and n is an integer from 0 to 40, m is an integer from 1 to 20, o is an integer from 1 to 40, and wherein a population of at least 20 percent of the recombinant vectors comprise a randomized nucleic acid sequence in which CorAA is a codon encoding for cysteine and a subset of said population has a codon encoding an amino acid other than histidine that immediately precedes the CorAA codon.

7. The set of recombinant vectors of claim 6, wherein the vector further comprises an endogenous gene of a replicating entity and the randomized nucleic acid sequence is located adjacent to the endogenous gene.

8. A set of randomized oligonucleotides, each oligonucleotide having the structure

[NXX]n [CorAA] [NXX]m [NZZ]o, or

[NZZ]o [NXX]m [CorAA] [NXX]n wherein each NXX is independently a randomized codon encoding for any amino acid except cysteine, CorAA is a codon encoding for cysteine or at least one other amino acid, each NZZ is independently a randomized codon encoding for any amino acid, and n is an integer from 0 to 40, m is an integer from 1 to 20, o is an integer from 1 to 40, and wherein in a population of at least 20 percent of the randomized oligonucleotides the CorAA codon encodes for cysteine and preceding in a subset of said population the codon immediately preceding the CorAA codon encodes an amino acid other than histidine.

9. The set of randomized oligonucleotides according to claim 8, wherein each codon encodes for a different amino acid.

10. The set of randomized oligonucleotides according to claim 8, wherein each NXX and NZZ individually is one codon selected from each group, namely group 1 consisting of GCT, GCC, GCA, and GCG, group 2 consisting of TTA, TTG, CTT, CTC, CTA, and CTG, group 3 consisting of CGT, CGC, CGA, CGG, AGA, and AGG, group 4 consisting of AAA and AAG, group 5 consisting of AAT and AAC, group 6 consisting of ATG, group 7 consisting of GAT and GAC, group 8 consisting of TTT and TTC, group 9 consisting of CCT, CCC, CCA and CCG, group 10 consisting of CAA and CAG, group 11 consisting of TCT, TCC, TCA, TCG, AGT and AGC, group 12 consisting of GAA and GAG, group 13 consisting of ACT, ACC, ACA and ACG, group 14 consisting of GGT, GGC, GGA and GGG, group 15 consisting of TGG, group 16 consisting of CAT and CAC, group 17 consisting of TAT and TAC, group 18 consisting of ATT, ATC and ATA, group 19 consisting of GTT, GTC, GTA and GTG and group 20 consisting of TGT and TGC.

11. The set of randomized oligonucleotides according to claim 8, wherein each NXX and NZZ individually is one codon selected from each group, namely group 1 consisting of GCT, GCC, GCA, and GCG, group 2 consisting of TTA, TTG, CTT, CTC, CTA, and CTG, group 3 consisting of CGT, CGC, CGA, CGG, AGA, and AGG, group 4 consisting of AAA and AAG, group 5 consisting of AAT and AAC, group 7 consisting of GAT and GAC, group 8 consisting of TTT and TTC, group 9 consisting of CCT, CCC, CCA and CCG, group 10 consisting of CAA and CAG, group 11 consisting of TCT, TCC, TCA, TCG, AGT and AGC, group 12 consisting of GAA and GAG, group 13 consisting of ACT, ACC, ACA and ACG, group 14 consisting of GGT, GGC, GGA and GGG, group 16 consisting of CAT and CAC, group 17 consisting of TAT and TAC, group 18 consisting of ATT, ATC and ATA, group 19 consisting of GTT, GTC, GTA and GTG and group 20 consisting of TGT and TGC.

12. A method for generating a library of replicating entities comprising the steps
 providing a set of randomized oligonucleotides according to claim 8,
 introducing each oligonucleotide into a replicating entity, and
 propagating the replicating entities as individual clones.

13. The method of claim 12, wherein introducing the oligonucleotide into the replicating entity comprises incorporating the oligonucleotide into a recombinant vector comprising an endogenous gene of the replicating entity such that the oligonucleotide is located adjacent to the endogenous gene.

14. A method for identifying an amino acid polymer able to interact with a target, comprising the steps
 providing a library of replicating entities according to claim 1,
 bringing the library into contact with the target, and
 enriching the replicating entities interacting with the target.

15. A method for generating a library of replicating entities which comprises using of a set of randomized oligonucleotides according to claim 8 to generate the library of replicating entities.

16. The library of claim 1, wherein the replicating entity is a prokaryotic cell, a eukaryotic cell, or a bacteriophage.

17. The library of claim 1, wherein CorAA is a codon encoding for cysteine or serine.

* * * * *

SEQUENCE LISTING

```
<160> NUMBER OF SEQ ID NOS: 142

<210> SEQ ID NO 1
<211> LENGTH: 29
<212> TYPE: DNA
<213> ORGANISM: Artificial Sequence
<220> FEATURE:
<221> NAME/KEY: source
<222> LOCATION: 1..29
<223> OTHER INFORMATION: /organism="Artificial Sequence"
      /note="oligonucleotide"
      /mol_type="unassigned DNA"

<400> SEQUENCE: 1
ggcgggctcg aagatctgcc attcatccg                                    29

<210> SEQ ID NO 2
<211> LENGTH: 29
<212> TYPE: DNA
<213> ORGANISM: Artificial Sequence
<220> FEATURE:
<221> NAME/KEY: source
<222> LOCATION: 1..29
<223> OTHER INFORMATION: /organism="Artificial Sequence"
      /note="oligonucleotide"
      /mol_type="unassigned DNA"

<400> SEQUENCE: 2
cggatgaatg gcagatcttc gagcccgcc                                    29

<210> SEQ ID NO 3
<211> LENGTH: 32
<212> TYPE: DNA
<213> ORGANISM: Artificial Sequence
```

```
<220> FEATURE:
<221> NAME/KEY: source
<222> LOCATION: 1..32
<223> OTHER INFORMATION: /organism="Artificial Sequence"
      /note="oligonucleotide"
      /mol_type="unassigned DNA"

<400> SEQUENCE: 3
gatcttccgt cacagatctt tattcgaaga cg                            32

<210> SEQ ID NO 4
<211> LENGTH: 32
<212> TYPE: DNA
<213> ORGANISM: Artificial Sequence
<220> FEATURE:
<221> NAME/KEY: source
<222> LOCATION: 1..32
<223> OTHER INFORMATION: /organism="Artificial Sequence"
      /note="oligonucleotide"
      /mol_type="unassigned DNA"

<400> SEQUENCE: 4
cgtcttcgaa taaagatctg tgacggaaga tc                            32

<210> SEQ ID NO 5
<211> LENGTH: 29
<212> TYPE: DNA
<213> ORGANISM: Artificial Sequence
<220> FEATURE:
<221> NAME/KEY: source
<222> LOCATION: 1..29
<223> OTHER INFORMATION: /organism="Artificial Sequence"
      /note="oligonucleotide"
      /mol_type="unassigned DNA"

<400> SEQUENCE: 5
ccacgctcac cggcaccaga tttatcagc                               29

<210> SEQ ID NO 6
<211> LENGTH: 29
<212> TYPE: DNA
<213> ORGANISM: Artificial Sequence
<220> FEATURE:
<221> NAME/KEY: source
<222> LOCATION: 1..29
<223> OTHER INFORMATION: /organism="Artificial Sequence"
      /note="oligonucleotide"
      /mol_type="unassigned DNA"

<400> SEQUENCE: 6
gctgataaat ctggtgccgg tgagcgtgg                               29

<210> SEQ ID NO 7
<211> LENGTH: 32
<212> TYPE: DNA
<213> ORGANISM: Artificial Sequence
<220> FEATURE:
<221> NAME/KEY: source
<222> LOCATION: 1..32
<223> OTHER INFORMATION: /organism="Artificial Sequence"
      /note="oligonucleotide"
      /mol_type="unassigned DNA"

<400> SEQUENCE: 7
catgcagctc ctcgagtcgg tcacagcttg tc                            32

<210> SEQ ID NO 8
<211> LENGTH: 32
<212> TYPE: DNA
```

```
<213> ORGANISM: Artificial Sequence
<220> FEATURE:
<221> NAME/KEY: source
<222> LOCATION: 1..32
<223> OTHER INFORMATION: /organism="Artificial Sequence"
      /note="oligonucleotide"
      /mol_type="unassigned DNA"

<400> SEQUENCE: 8
gacaagctgt gaccgactcg aggagctgca tg                          32

<210> SEQ ID NO 9
<211> LENGTH: 31
<212> TYPE: DNA
<213> ORGANISM: Artificial Sequence
<220> FEATURE:
<221> NAME/KEY: source
<222> LOCATION: 1..31
<223> OTHER INFORMATION: /organism="Artificial Sequence"
      /note="oligonucleotide"
      /mol_type="unassigned DNA"

<400> SEQUENCE: 9
gctgcaatga taccgcgcga cccacgctca c                           31

<210> SEQ ID NO 10
<211> LENGTH: 31
<212> TYPE: DNA
<213> ORGANISM: Artificial Sequence
<220> FEATURE:
<221> NAME/KEY: source
<222> LOCATION: 1..31
<223> OTHER INFORMATION: /organism="Artificial Sequence"
      /note="oligonucleotide"
      /mol_type="unassigned DNA"

<400> SEQUENCE: 10
gtgagcgtgg gtcgcgcggt atcattgcag c                           31

<210> SEQ ID NO 11
<211> LENGTH: 47
<212> TYPE: DNA
<213> ORGANISM: Artificial Sequence
<220> FEATURE:
<221> NAME/KEY: source
<222> LOCATION: 1..47
<223> OTHER INFORMATION: /organism="Artificial Sequence"
      /note="oligonucleotide"
      /mol_type="unassigned DNA"

<400> SEQUENCE: 11
gcttcaataa tattgaaaaa ggatgagtat gagtattcaa catttcc          47

<210> SEQ ID NO 12
<211> LENGTH: 47
<212> TYPE: DNA
<213> ORGANISM: Artificial Sequence
<220> FEATURE:
<221> NAME/KEY: source
<222> LOCATION: 1..47
<223> OTHER INFORMATION: /organism="Artificial Sequence"
      /note="oligonucleotide"
      /mol_type="unassigned DNA"

<400> SEQUENCE: 12
ggaaatgttg aatactcata ctcatccttt ttcaatatta ttgaagc          47

<210> SEQ ID NO 13
<211> LENGTH: 35
```

```
<212> TYPE: DNA
<213> ORGANISM: Artificial Sequence
<220> FEATURE:
<221> NAME/KEY: source
<222> LOCATION: 1..35
<223> OTHER INFORMATION: /organism="Artificial Sequence"
      /note="oligonucleotide"
      /mol_type="unassigned DNA"

<400> SEQUENCE: 13
aatttccaca ccactggtga gtgagctgat accgc                              35

<210> SEQ ID NO 14
<211> LENGTH: 29
<212> TYPE: DNA
<213> ORGANISM: Artificial Sequence
<220> FEATURE:
<221> NAME/KEY: source
<222> LOCATION: 1..29
<223> OTHER INFORMATION: /organism="Artificial Sequence"
      /note="oligonucleotide"
      /mol_type="unassigned DNA"

<400> SEQUENCE: 14
aatttgccgg ctcgcgcgtt tcggtgatg                                     29

<210> SEQ ID NO 15
<211> LENGTH: 33
<212> TYPE: DNA
<213> ORGANISM: Artificial Sequence
<220> FEATURE:
<221> NAME/KEY: source
<222> LOCATION: 1..33
<223> OTHER INFORMATION: /organism="Artificial Sequence"
      /note="oligonucleotide"
      /mol_type="unassigned DNA"

<400> SEQUENCE: 15
gtttcgctac cgtagtgcag gccggcgata atg                                33

<210> SEQ ID NO 16
<211> LENGTH: 33
<212> TYPE: DNA
<213> ORGANISM: Artificial Sequence
<220> FEATURE:
<221> NAME/KEY: source
<222> LOCATION: 1..33
<223> OTHER INFORMATION: /organism="Artificial Sequence"
      /note="oligonucleotide"
      /mol_type="unassigned DNA"

<400> SEQUENCE: 16
cattatcgcc ggcctgcact acggtagcga aac                                33

<210> SEQ ID NO 17
<211> LENGTH: 31
<212> TYPE: DNA
<213> ORGANISM: Artificial Sequence
<220> FEATURE:
<221> NAME/KEY: source
<222> LOCATION: 1..31
<223> OTHER INFORMATION: /organism="Artificial Sequence"
      /note="oligonucleotide"
      /mol_type="unassigned DNA"

<400> SEQUENCE: 17
cgatcaactg ggtgcgagcg tggtggtgtc g                                  31

<210> SEQ ID NO 18
```

```
<211> LENGTH: 31
<212> TYPE: DNA
<213> ORGANISM: Artificial Sequence
<220> FEATURE:
<221> NAME/KEY: source
<222> LOCATION: 1..31
<223> OTHER INFORMATION: /organism="Artificial Sequence"
      /note="oligonucleotide"
      /mol_type="unassigned DNA"

<400> SEQUENCE: 18
cgacaccacc acgctcgcac ccagttgatc g                              31

<210> SEQ ID NO 19
<211> LENGTH: 32
<212> TYPE: DNA
<213> ORGANISM: Artificial Sequence
<220> FEATURE:
<221> NAME/KEY: source
<222> LOCATION: 1..32
<223> OTHER INFORMATION: /organism="Artificial Sequence"
      /note="oligonucleotide"
      /mol_type="unassigned DNA"

<400> SEQUENCE: 19
gctgaattac attccgaacc gcgtggcaca ac                             32

<210> SEQ ID NO 20
<211> LENGTH: 32
<212> TYPE: DNA
<213> ORGANISM: Artificial Sequence
<220> FEATURE:
<221> NAME/KEY: source
<222> LOCATION: 1..32
<223> OTHER INFORMATION: /organism="Artificial Sequence"
      /note="oligonucleotide"
      /mol_type="unassigned DNA"

<400> SEQUENCE: 20
gttgtgccac gcggttcgga atgtaattca gc                             32

<210> SEQ ID NO 21
<211> LENGTH: 40
<212> TYPE: DNA
<213> ORGANISM: Artificial Sequence
<220> FEATURE:
<221> NAME/KEY: source
<222> LOCATION: 1..40
<223> OTHER INFORMATION: /organism="Artificial Sequence"
      /note="oligonucleotide"
      /mol_type="unassigned DNA"

<400> SEQUENCE: 21
ggatgccatt gctgtcgaag ctgcgtgcac taatgttccg                     40

<210> SEQ ID NO 22
<211> LENGTH: 40
<212> TYPE: DNA
<213> ORGANISM: Artificial Sequence
<220> FEATURE:
<221> NAME/KEY: source
<222> LOCATION: 1..40
<223> OTHER INFORMATION: /organism="Artificial Sequence"
      /note="oligonucleotide"
      /mol_type="unassigned DNA"

<400> SEQUENCE: 22
cggaacatta gtgcacgcag cttcgacagc aatggcatcc                     40
```

```
<210> SEQ ID NO 23
<211> LENGTH: 32
<212> TYPE: DNA
<213> ORGANISM: Artificial Sequence
<220> FEATURE:
<221> NAME/KEY: source
<222> LOCATION: 1..32
<223> OTHER INFORMATION: /organism="Artificial Sequence"
      /note="oligonucleotide"
      /mol_type="unassigned DNA"

<400> SEQUENCE: 23
atttctagat ctaccgtatt accgcctttg ag                               32

<210> SEQ ID NO 24
<211> LENGTH: 33
<212> TYPE: DNA
<213> ORGANISM: Artificial Sequence
<220> FEATURE:
<221> NAME/KEY: source
<222> LOCATION: 1..33
<223> OTHER INFORMATION: /organism="Artificial Sequence"
      /note="oligonucleotide"
      /mol_type="unassigned DNA"

<400> SEQUENCE: 24
aatttgaatt cagctgtttc ctgtgtgaaa ttg                              33

<210> SEQ ID NO 25
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /organism="Artificial Sequence"
      /note="oligonucleotide"
      /mol_type="unassigned DNA"

<400> SEQUENCE: 25
tgcggatatc tcggtagtgg                                             20

<210> SEQ ID NO 26
<211> LENGTH: 51
<212> TYPE: DNA
<213> ORGANISM: Artificial Sequence
<220> FEATURE:
<221> NAME/KEY: source
<222> LOCATION: 1..51
<223> OTHER INFORMATION: /organism="Artificial Sequence"
      /note="oligonucleotide"
      /mol_type="unassigned DNA"

<400> SEQUENCE: 26
attgggcgcc agggtggttt ttcttttcac cagtgacacg ggcaacagct g          51

<210> SEQ ID NO 27
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /organism="Artificial Sequence"
      /note="oligonucleotide"
      /mol_type="unassigned DNA"

<400> SEQUENCE: 27
aattccaggt acatggagct cactgcccgc tttcc                            35
```

<210> SEQ ID NO 28
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /organism="Artificial Sequence"
    /note="oligonucleotide"
    /mol_type="unassigned DNA"

<400> SEQUENCE: 28
ccaaggaggt ctagataacg agggagatct atgaaaaaga cagctatcgc         50

<210> SEQ ID NO 29
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /organism="Artificial Sequence"
    /note="oligonucleotide"
    /mol_type="unassigned DNA"

<400> SEQUENCE: 29
gcgatagctg tcttttttcat agatctccct cgttatctag acctccttgg         50

<210> SEQ ID NO 30
<211> LENGTH: 30
<212> TYPE: DNA
<213> ORGANISM: Artificial Sequence
<220> FEATURE:
<221> NAME/KEY: source
<222> LOCATION: 1..30
<223> OTHER INFORMATION: /organism="Artificial Sequence"
    /note="oligonucleotide"
    /mol_type="unassigned DNA"

<400> SEQUENCE: 30
ttaattcgaa accgtattac cgcctttgag                                 30

<210> SEQ ID NO 31
<211> LENGTH: 23
<212> TYPE: DNA
<213> ORGANISM: Artificial Sequence
<220> FEATURE:
<221> NAME/KEY: source
<222> LOCATION: 1..23
<223> OTHER INFORMATION: /organism="Artificial Sequence"
    /note="oligonucleotide"
    /mol_type="unassigned DNA"

<400> SEQUENCE: 31
ttaagatatc cgcaccaacg cgc                                        23

<210> SEQ ID NO 32
<211> LENGTH: 57
<212> TYPE: DNA
<213> ORGANISM: Artificial Sequence
<220> FEATURE:
<221> NAME/KEY: source
<222> LOCATION: 1..57
<223> OTHER INFORMATION: /organism="Artificial Sequence"
    /note="oligonucleotide"
    /mol_type="unassigned DNA"

<400> SEQUENCE: 32
tttaatcgcg atagctgtct ttttcatttt ttgccctcgt gtgaaattgt tatccgc   57

```
<210> SEQ ID NO 33
<211> LENGTH: 18
<212> TYPE: DNA
<213> ORGANISM: Artificial Sequence
<220> FEATURE:
<221> NAME/KEY: source
<222> LOCATION: 1..18
<223> OTHER INFORMATION: /organism="Artificial Sequence"
      /note="oligonucleotide"
      /mol_type="unassigned DNA"

<400> SEQUENCE: 33
gtgtcgacgt ctcccggc                                                   18

<210> SEQ ID NO 34
<211> LENGTH: 19
<212> TYPE: DNA
<213> ORGANISM: Artificial Sequence
<220> FEATURE:
<221> NAME/KEY: source
<222> LOCATION: 1..19
<223> OTHER INFORMATION: /organism="Artificial Sequence"
      /note="oligonucleotide"
      /mol_type="unassigned DNA"

<400> SEQUENCE: 34
acgtctccct ccgctggag                                                  19

<210> SEQ ID NO 35
<211> LENGTH: 18
<212> TYPE: DNA
<213> ORGANISM: Artificial Sequence
<220> FEATURE:
<221> NAME/KEY: source
<222> LOCATION: 1..18
<223> OTHER INFORMATION: /organism="Artificial Sequence"
      /note="oligonucleotide"
      /mol_type="unassigned DNA"

<400> SEQUENCE: 35
gtgtcgacgt ctcccggc                                                   18

<210> SEQ ID NO 36
<211> LENGTH: 18
<212> TYPE: DNA
<213> ORGANISM: Artificial Sequence
<220> FEATURE:
<221> NAME/KEY: source
<222> LOCATION: 1..18
<223> OTHER INFORMATION: /organism="Artificial Sequence"
      /note="oligonucleotide"
      /mol_type="unassigned DNA"

<400> SEQUENCE: 36
ctgtcgacgt ctccctcc                                                   18

<210> SEQ ID NO 37
<211> LENGTH: 90
<212> TYPE: DNA
<213> ORGANISM: Artificial Sequence
<220> FEATURE:
<221> NAME/KEY: source
<222> LOCATION: 1..90
<223> OTHER INFORMATION: /organism="Artificial Sequence"
      /note="oligonucleotide"
      /mol_type="unassigned DNA"
<220> FEATURE:
<221> NAME/KEY: misc_feature
<222> LOCATION: 19..27
```

```
<223> OTHER INFORMATION: /note="n is a, c, g, or t"
<220> FEATURE:
<221> NAME/KEY: misc_feature
<222> LOCATION: 31..49
<223> OTHER INFORMATION: /note="n is a, c, g, or t"
<220> FEATURE:
<221> NAME/KEY: misc_feature
<222> LOCATION: 52..65
<223> OTHER INFORMATION: /note="n is a, c, g, or t"

<400> SEQUENCE: 37
gtgtcgacgt ctcccggcnn nnnnnntsc nnnnnnnnnn nnnnnnnnny ynnnnnnnn      60 nnnnnctcca gcggagggag acgtcgacag                                    90

<210> SEQ ID NO 38
<211> LENGTH: 90
<212> TYPE: DNA
<213> ORGANISM: Artificial Sequence
<220> FEATURE:
<221> NAME/KEY: source
<222> LOCATION: 1..90
<223> OTHER INFORMATION: /organism="Artificial Sequence"
      /note="oligonucleotide"
      /mol_type="unassigned DNA"
<220> FEATURE:
<221> NAME/KEY: misc_feature
<222> LOCATION: 19..27
<223> OTHER INFORMATION: /note="n is a, c, g, or t"
<220> FEATURE:
<221> NAME/KEY: misc_feature
<222> LOCATION: 31..49
<223> OTHER INFORMATION: /note="n is a, c, g, or t"
<220> FEATURE:
<221> NAME/KEY: misc_feature
<222> LOCATION: 52..65
<223> OTHER INFORMATION: /note="n is a, c, g, or t"

<400> SEQUENCE: 38
cacagctgca gagggccgnn nnnnnnasg nnnnnnnnnn nnnnnnnnny ynnnnnnnn      60 nnnnngtggt cgcctccctc tgcagctgtc                                    90

<210> SEQ ID NO 39
<211> LENGTH: 126
<212> TYPE: DNA
<213> ORGANISM: Artificial Sequence
<220> FEATURE:
<221> NAME/KEY: source
<222> LOCATION: 1..126
<223> OTHER INFORMATION: /organism="Artificial Sequence"
      /note="oligonucleotide"
      /mol_type="unassigned DNA"
<220> FEATURE:
<221> NAME/KEY: misc_feature
<222> LOCATION: 19..33
<223> OTHER INFORMATION: /note="n is a, c, g, or t"
<220> FEATURE:
<221> NAME/KEY: misc_feature
<222> LOCATION: 82..108
<223> OTHER INFORMATION: /note="n is a, c, g, or t"

<400> SEQUENCE: 39
gtgtcgacgt ctcccggcnn nnnnnnnnn nnntstgttg ttgcaggcac tgcacgccgt     60
gcaggcaccg tcggtgtcts tnnnnnnnnn nnnnnnnnnn nnnnnnnngg agggagacgt   120
cgacag                                                             126

<210> SEQ ID NO 40
<211> LENGTH: 126
<212> TYPE: DNA
<213> ORGANISM: Artificial Sequence
```

```
<220> FEATURE:
<221> NAME/KEY: source
<222> LOCATION: 1..126
<223> OTHER INFORMATION: /organism="Artificial Sequence"
      /note="oligonucleotide"
      /mol_type="unassigned DNA"
<220> FEATURE:
<221> NAME/KEY: misc_feature
<222> LOCATION: 19..33
<223> OTHER INFORMATION: /note="n is a, c, g, or t"
<220> FEATURE:
<221> NAME/KEY: misc_feature
<222> LOCATION: 82..108
<223> OTHER INFORMATION: /note="n is a, c, g, or t"

<400> SEQUENCE: 40
cacagctgca gagggccgnn nnnnnnnnnn nnnasacaac aacgtccgtg acgtgcggca      60
cgtccgtggc agccacagas annnnnnnnn nnnnnnnnnn nnnnnnnncc tccctctgca    120
gctgtc                                                               126

<210> SEQ ID NO 41
<211> LENGTH: 28
<212> TYPE: PRT
<213> ORGANISM: Artificial Sequence
<220> FEATURE:
<223> OTHER INFORMATION: amino acid polymer

<400> SEQUENCE: 41

Val Val Gln Ala Gly Asn Asn Asn Cys Asn Asn Asn Asn Asn Asn
1               5                   10                  15

Asn Asn Asn Asn Asn Ser Ser Pro Val Gly Thr Ala
                20                  25

<210> SEQ ID NO 42
<211> LENGTH: 83
<212> TYPE: DNA
<213> ORGANISM: Artificial Sequence
<220> FEATURE:
<221> NAME/KEY: source
<222> LOCATION: 1..83
<223> OTHER INFORMATION: /organism="Artificial Sequence"
      /note="oligonucleotide"
      /mol_type="unassigned DNA"
<220> FEATURE:
<221> NAME/KEY: misc_feature
<222> LOCATION: 17..25
<223> OTHER INFORMATION: /note="n is a, c, g, or t"
<220> FEATURE:
<221> NAME/KEY: misc_feature
<222> LOCATION: 29..44
<223> OTHER INFORMATION: /note="n is a, c, g, or t"
<220> FEATURE:
<221> NAME/KEY: misc_feature
<222> LOCATION: 47..60
<223> OTHER INFORMATION: /note="n is a, c, g, or t"

<400> SEQUENCE: 42
cgtagtgcag gccggcnnnn nnnntscnn nnnnnnnnnn nnnyynnnnn nnnnnnnnnn       60
ctccagccca gtgggtaccg ctg                                             83

<210> SEQ ID NO 43
<211> LENGTH: 83
<212> TYPE: DNA
<213> ORGANISM: Artificial Sequence
<220> FEATURE:
<221> NAME/KEY: source
<222> LOCATION: 1..83
<223> OTHER INFORMATION: /organism="Artificial Sequence"
      /note="oligonucleotide"
```

```
        /mol_type="unassigned DNA"
<220> FEATURE:
<221> NAME/KEY: misc_feature
<222> LOCATION: 17..25
<223> OTHER INFORMATION: /note="n is a, c, g, or t"
<220> FEATURE:
<221> NAME/KEY: misc_feature
<222> LOCATION: 29..44
<223> OTHER INFORMATION: /note="n is a, c, g, or t"
<220> FEATURE:
<221> NAME/KEY: misc_feature
<222> LOCATION: 47..60
<223> OTHER INFORMATION: /note="n is a, c, g, or t"

<400> SEQUENCE: 43
gcatcacgtc cggccgnnnn nnnnnawgnn nnnnnnnnnn nnnnyynnnn nnnnnnnnnn    60
gaggtcgggt cacccatggc gac                                            83

<210> SEQ ID NO 44
<211> LENGTH: 4566
<212> TYPE: DNA
<213> ORGANISM: Artificial Sequence
<220> FEATURE:
<221> NAME/KEY: source
<222> LOCATION: 1..4566
<223> OTHER INFORMATION: /organism="Artificial Sequence"
      /note="oligonucleotide"
      /mol_type="unassigned DNA"

<400> SEQUENCE: 44
aattcacctc gaaagcaagc tgataaaccg atacaattaa aggctccttt tggagccttt    60
ttttttggag attttcaacg tgaaaaaatt attattcgca attccaagct aattcacctc   120
gaaagcaagc tgataaaccg atacaattaa aggctccttt tggagccttt ttttttggag   180
attttcaacg tgaaaaaatt attattcgca attccaagct ctgcctcgcg cgtttcggtg   240
atgacggtga aacctctga cacatgcagc tcctcgagtc ggtcacagct tgtctgtaag    300
cggatgcaga tcacgcgccc tgtagcggcg cattaagcgc ggcgggtgtg gtggttacgc    360
gcagcgtgac cgctacactt gccagcgccc tagcgcccgc tcctttcgct ttcttccctt    420
cctttctcgc cacgttcgcc agctttcccc gtcaagctct aaatcggggg ctccctttag    480
ggttccgatt tagtgcttta cggcacctcg accccaaaaa acttgattag ggtgatggtt    540
cacgtagtgg gccatcgccc tgatagacgg ttttcgccc tttgacgttg gagtccacgt     600
tctttaatag tggactcttg ttccaaactg gaacaacact caaccctatc tcggtctatt    660
cttttgattt ataagggatt tgccgatttt cggcctattg gttaaaaaat gagctgattt    720
aacaaaaatt taacgcgaat tttaacaaaa tattaacgtt tacaatttga tctgcgctcg    780
gtcgttcggc tgcggcgagc ggtatcagct cactcaaagg cggtaatacg gttatccaca    840
gaatcagggg ataacgcagg aaagaacatg tgagcaaaag gccagcaaaa ggccaggaac    900
cgtaaaaagg ccgcgttgct ggcgttttc cataggctcc gcccccctga cgagcatcac     960
aaaaatcgac gctcaagtca gaggtggcga aacccgacag gactataaag ataccaggcg   1020
tttccccctg gaagctccct cgtgcgctct cctgttccga ccctgccgct taccggatac    1080
ctgtccgcct ttctcccttc gggaagcgtg gcgctttctc aatgctcacg ctgtaggtat    1140
ctcagttcgg tgtaggtcgt tcgctccaag ctgggctgtg tgcacgaacc ccccgttcag    1200
cccgaccgct gcgccttatc cggtaactat cgtcttgagt ccaacccggt aagacacgac    1260
ttatcgccac tggcagcagc cactggtaac aggattagca gagcgaggta tgtaggcggt    1320
gctacagagt tcttgaagtg gtggcctaac tacggctaca ctagaaggac agtatttggt    1380
```

```
atctgcgctc tgctgaagcc agttaccttc ggaaaaagag ttggtagctc ttgatccggc    1440
aaacaaacca ccgctggtag cggtggtttt tttgtttgca agcagcagat tacgcgcaga    1500
aaaaaaggat ctcaagaaga tcctttgatc ttttctacgg ggtctgacgc tcagtggaac    1560
gaaaactcac gttaagggat tttggtcatg agattatcaa aaaggatctt cacctagatc    1620
cttttaaatt aaaaatgaag ttttaaatca atctaaagta tatatgagta aacttggtct    1680
gacagttacc aatgcttaat cagtgaggca cctatctcag cgatctgtct atttcgttca    1740
tccatagttg cctgactccc cgtcgtgtag ataactacga tacgggaggg cttaccatct    1800 ggccccagtgc tgcaatgata ccgcgcgacc cacgctcacc ggcaccagat ttatcagcaa    1860
taaaccagcc agccggaagg gccgagcgca gaagtggtcc tgcaacttta tccgcctcca    1920
tccagtctat taattgttgc cgggaagcta gagtaagtag ttcgccagtt aatagtttgc    1980
gcaacgttgt tgccattgct gcaggcatcg tggtgtcacg ctcgtcgttt ggtatggctt    2040
cattcagctc cggttcccaa cgatcaaggc gagttacatg atcccccatg ttgtgcaaaa    2100
aagcggttag ctccttcggt cctccgatcg ttgtcagaag taagttggcc gcagtgttat    2160
cactcatggt tatggcagca ctgcataatt ctcttactgt catgccatcc gtaagatgct    2220
tttctgtgac tggtgagtac tcaaccaagt cattctgaga atagtgtatg cggcgaccga    2280
gttgctcttg cccggcgtca cacgggata ataccgcgcc acatagcaga actttaaaag    2340
tgctcatcat tggaaaacgt tcttcggggc gaaaactctc aaggatctta ccgctgttga    2400
gatccagttc gatgtaaccc actcgtgcac ccaactgatc ttcagcatct tttactttca    2460
ccagcgtttc tgggtgagca aaaacaggaa ggcaaaatgc cgcaaaaaag ggaataaggg    2520
cgacacggaa atgttgaata ctcatactca tccttttca atattattga agcagacagt    2580
tttattgttc atgatgatat attttatct tgtgcaatgt aacatcagag attttgagac    2640
acaacgtggc tttgttgaat aaatcgaact tttgctgagt tgactcccg cgcgcgatgg    2700 gtcgaatttg ctttcgaaaa aaagcccgc tcattaggcg ggctaaaaaa aagcccgctc    2760
attaggcggg ctcgaagatc tttattcgaa gacgaaaggg catcgcgcgc ggggaattgg    2820
ccacgatgcg tccggcgtag aggatctctc acctaccaaa caatgccccc ctgcaaaaaa    2880
taaattcata taaaaaacat atagataacc atctgcggtg ataaattatc tctggcggtg    2940
ttgacataaa taccactggc ggtgatactg agcacatcag caggacgcac tgaccaccat    3000
gaaggtgacg ctcttaaaat taagccctga agaagggcag cattcaaagc agaaggcttt    3060
ggggtgtgtg atacgaaacg aagcattgga attctacaac ttgcttggat cctacaaag    3120 aagcagcaat tttcagtgtc agaagtcgac caaggaggtc tagataacga ggcgcaaaaa    3180
atgaaaaaga cagctatcgc gattgcagtg gcactgctg gtttcgctac cgtagtgcag    3240
gccggctacg gtcagtgctg gtttccaggt gaatgccgtc catgcgctga aaactccagc    3300
ggaggtggca ccagtggtgt gggtaccgct gaaactgttg aaagttgttt agcaaaaccc    3360
catacagaaa attcatttac taacgtctgg aaagacgaca aaactttaga tcgttacgct    3420
aactatgagg ttgtctgtg gaatgctaca ggcgttgtag tttgtactgg tgacgaaact    3480
cagtgttacg gtacatgggt tcctattggg cttgctatcc ctgaaaatga gggtggtggc    3540
tctgagggtg gcggttctga gggtggcggt tctgagggtg gcggtaccaa acctcctgag    3600
tacggtgata cacctattcc gggctatact tatatcaacc ctctcgacgg cacttatccg    3660
cctggtactg agcaaaaccc cgctaatcct aatccttctc ttgaggagtc tcagcctctt    3720
```

```
aatactttca tgtttcagaa taataggttc cgaaataggc aggggcatt aactgtttat    3780 acgggcactg ttactcaagg cactgacccc gttaaaactt attaccagta cactcctgta    3840
tcatcaaaag ccatgtatga cgcttactgg aacggtaaat tcagagactg cgctttccat    3900
tctggcttta atgaggatcc attcgtttgt gaatatcaag gccaatcgtc tgacctgcct    3960
caacctcctg tcaatgctgg cggcggctct ggtggtggtt ctggtggcgg ctctgagggt    4020
ggtggctctg agggtggcgg ttctgagggt ggcggctctg agggaggcgg ttccggtggt    4080
ggctctggtt ccggtgattt tgattatgaa aagatggcaa acgctaataa gggggctatg    4140
accgaaaatg ccgatgaaaa cgcgctacag tctgacgcta aaggcaaact tgattctgtc    4200
gctactgatt acggtgctgc tatcgatggt ttcattggtg acgtttccgg ccttgctaat    4260
ggtaatggtg ctactggtga ttttgctggc tctaattccc aaatggctca agtcggtgac    4320
ggtgataatt cacctttaat gaataatttc cgtcaatatt taccttccct ccctcaatcg    4380
gttgaatgtc gcccttttgt ctttagcgct ggtaaaccat atgaatttc tattgattgt    4440 gacaaaataa acttattccg tggtgtcttt gcgtttcttt tatatgttgc cacctttatg    4500
tatgtatttt ctacgtttgc taacatactg cgtaataagg agtcttaagc ttggtctaga    4560
ggtcga                                                              4566

<210> SEQ ID NO 45
<211> LENGTH: 5539
<212> TYPE: DNA
<213> ORGANISM: Artificial Sequence
<220> FEATURE:
<221> NAME/KEY: source
<222> LOCATION: 1..5539
<223> OTHER INFORMATION: /organism="Artificial Sequence"
      /note="oligonucleotide"
      /mol_type="unassigned DNA"

<400> SEQUENCE: 45
aattcacctc gaaagcaagc tgataaaccg atacaattaa aggctccttt tggagccttt      60 tttttggag atttcaacg tgaaaaaatt attattcgca attccaagct aattcaccctc     120 gaaagcaagc tgataaaccg atacaattaa aggctccttt tggagccttt tttttggag     180 attttcaacg tgaaaaaatt attattcgca attccaagct ctgcctcgcg cgtttcggtg     240
atgacggtga aaacctctga cacatgcagc tcctcgagtc ggtcacagct tgtctgtaag     300
cggatgcaga tcacgcgccc tgtagcggcg cattaagcgc ggcgggtgtg gtggttacgc     360
gcagcgtgac cgctacactt gccagcgccc tagcgcccgc tcctttcgct ttcttccctt     420
cctttctcgc cacgttcgcc agctttcccc gtcaagctct aaatcggggg ctccctttag     480
ggttccgatt tagtgcttta cggcacctcg accccaaaaa acttgattag ggtgatggtt     540
cacgtagtgg gccatcgccc tgatagacgg ttttcgccc tttgacgttg agtccacgt     600 tctttaatag tggactcttg ttccaaactg gaacaacact caaccctatc tcggtctatt     660
cttttgattt ataagggatt ttgccgattt cggcctattg gttaaaaaat gagctgattt     720
aacaaaaatt taacgcgaat tttaacaaaa tattaacgtt tacaatttga tctgcgctcg     780
gtcgttcggc tgcggcgagc ggtatcagct cactcaaagg cggtaatacg gttatccaca     840
gaatcagggg ataacgcagg aaagaacatg tgagcaaaag gccagcaaaa ggccaggaac     900
cgtaaaaagg ccgcgttgct ggcgtttttc cataggctcc gcccccctga cgagcatcac     960
aaaaatcgac gctcaagtca gaggtggcga aacccgacag gactataaag ataccaggcg    1020
tttccccctg gaagctccct cgtgcgctct cctgttccga cctgccgct taccggatac    1080
```

```
ctgtccgcct ttctcccttc gggaagcgtg gcgctttctc aatgctcacg ctgtaggtat    1140
ctcagttcgg tgtaggtcgt tcgctccaag ctgggctgtg tgcacgaacc ccccgttcag    1200
cccgaccgct gcgccttatc cggtaactat cgtcttgagt ccaacccggt aagacacgac    1260
ttatcgccac tggcagcagc cactggtaac aggattagca gagcgaggta tgtaggcggt    1320
gctacagagt tcttgaagtg gtggcctaac tacggctaca ctagaaggac agtatttggt    1380
atctgcgctc tgctgaagcc agttaccttc ggaaaaagag ttggtagctc ttgatccggc    1440
aaacaaacca ccgctggtag cggtggtttt tttgtttgca agcagcagat tacgcgcaga    1500
aaaaaaggat ctcaagaaga tcctttgatc ttttctacgg ggtctgacgc tcagtggaac    1560
gaaaactcac gttaagggat tttggtcatg agattatcaa aaaggatctt cacctagatc    1620
cttttaaatt aaaaatgaag ttttaaatca atctaaagta tatatgagta aacttggtct    1680
gacagttacc aatgcttaat cagtgaggca cctatctcag cgatctgtct atttcgttca    1740
tccatagttg cctgactccc cgtcgtgtag ataactacga tacgggaggg cttaccatct    1800
ggcccagtgc tgcaatgata ccgcgcgacc cacgctcacc ggcaccagat ttatcagcaa    1860
taaaccagcc agccggaagg gccgagcgca gaagtggtcc tgcaacttta tccgcctcca    1920
tccagtctat taattgttgc cgggaagcta gagtaagtag ttcgccagtt aatagtttgc    1980
gcaacgttgt tgccattgct gcaggcatcg tggtgtcacg ctcgtcgttt ggtatggctt    2040
cattcagctc cggttcccaa cgatcaaggc gagttacatg atccccatg ttgtgcaaaa    2100 aagcggttag ctccttcggt cctccgatcg ttgtcagaag taagttggcc gcagtgttat    2160
cactcatggt tatggcagca ctgcataatt ctcttactgt catgccatcc gtaagatgct    2220
tttctgtgac tggtgagtac tcaaccaagt cattctgaga atagtgtatg cggcgaccga    2280
gttgctcttg cccggcgtca acacgggata ataccgcgcc acatagcaga actttaaaag    2340
tgctcatcat tggaaaacgt tcttcggggc gaaaactctc aaggatctta ccgctgttga    2400
gatccagttc gatgtaaccc actcgtgcac ccaactgatc ttcagcatct tttactttca    2460
ccagcgtttc tgggtgagca aaaacaggaa ggcaaaatgc cgcaaaaaag ggaataaggg    2520
cgacacggaa atgttgaata ctcatactca tccttttttca atattattga agcagacagt    2580
tttattgttc atgatgatat attttttatct tgtgcaatgt aacatcagag attttgagac    2640
acaacgtggc tttgttgaat aaatcgaact tttgctgagt tgactcccg cgcgcgatgg    2700 gtcgaatttg ctttcgaaac cgtattaccg cctttgagtg agctgatacc gctcgccgca    2760
gccgaacgac cgagcgcagc gagtcagtga gcgaggaagc ggaaactagc tagtgacacc    2820
atcgaatggc gcaaaacctt tcgcggtatg gcatgatagc gcccggaaga gagtcaattc    2880
agggtggtga atgtgaaacc agtaacgtta tacgatgtcg cagagtatgc cggtgtctct    2940
tatcagaccg tttcccgcgt ggtgaaccag gccagccacg tttctgcgaa aacgcgggaa    3000
aaagtggaag cggcgatggc ggagctgaat tacattccga accgcgtggc acaacaactg    3060
gcgggcaaac agtcgttgct gattggcgtt gccacctcga gtctggccct ccacgcgccg    3120
tcgcaaattg tcgcggcgat taaatctcgc gccgatcaac tgggtgcgag cgtggtggtg    3180
tcgatggtag aacgaagcgg cgtcgaagcc tgtaaagcgg cggtgcacaa tcttctcgcg    3240
cagagagtca gtgggctgat cattaactat ccgctggatg accaggatgc cattgctgtc    3300
gaagctgcgt gcactaatgt tccggcgtta tttcttgatg tctctgacca gacacccatc    3360
aacagtatta ttttctccca tgaagacggt acgcgactgg gcgtggagca tctggtcgca    3420
```

-continued

| | |
|---|---|
| ttgggtcacc agcaaatcgc gctgttagca ggtccgctgt cctctgtctc ggcgcgtctg | 3480 |
| cgtctggctg gctggcataa atatctcact cgcaatcaaa ttcagccgat agcggaacgg | 3540 |
| gaaggcgatt ggagtgccat gtccggtttt caacaaacca tgcaaatgct gaatgagggc | 3600 |
| atcgttccca ctgcgatgct ggttgccaac gatcagatgg cgctgggcgc aatgcgcgcc | 3660 |
| attaccgagt ccgggctgcg cgttggtgcg gatatctcgg tagtgggata cgacgatacc | 3720 |
| gaagacagct catgttatat cccgccgtta accaccatca aacaggattt tcgcctgctg | 3780 |
| gggcaaacca gcgtggaccg cttgctgcaa ctctctcagg gccaggcggt gaagggcaat | 3840 |
| cagctgttgc ccgtgtcact ggtgaaaaga aaaaccaccc tggcgcccaa tacgcaaacc | 3900 |
| gcctctcccc gcgcgttggc cgattcatta atgcagctgg cacgacaggt tccccgactg | 3960 |
| gaaagcgggc agtgagctcc atgtacccga taaaagcggc ttcctgacag gaggccgttt | 4020 |
| tgttttgcag cccacctgag ctcaacgcaa ttaatgtgag ttagctcact cattaggcac | 4080 |
| cccaggcttt acactttatg cttccggctc gtatgttgtg tggaattgtg agcggataac | 4140 |
| aatttcacac gagggcaaaa aatgaaaaag acagctatcg cgattgcagt ggcactggct | 4200 |
| ggtttcgcta ccgtagcgca ggccggccca cagatagttt actctcgtga ccatgaccat | 4260 |
| ctggacgttg aaggaggtgg caccagtggt gtgggtaccg ctgaaactgt tgaaagttgt | 4320 |
| ttagcaaaac cccatacaga aaattcattt actaacgtct ggaaagacga caaaacttta | 4380 |
| gatcgttacg ctaactatga gggctgtctg tggaatgcta caggcgttgt agtttgtact | 4440 |
| ggtgacgaaa ctcagtgtta cggtacatgg gttcctattg gcttgctat ccctgaaaat | 4500 |
| gagggtggtg gctctgaggg tggcggttct gagggtggcg ttctgaggg tggcggtacc | 4560 |
| aaacctcctg agtacggtga tacacctatt ccgggctata cttatatcaa ccctctcgac | 4620 |
| ggcacttatc cgcctggtac tgagcaaaac cccgctaatc ctaatccttc tcttgaggag | 4680 |
| tctcagcctc ttaatacttt catgtttcag aataataggt tccgaaatag cagggggca | 4740 |
| ttaactgttt atacgggcac tgttactcaa ggcactgacc ccgttaaaac ttattaccag | 4800 |
| tacactcctg tatcatcaaa agccatgtat gacgcttact ggaacggtaa attcagagac | 4860 |
| tgcgctttcc attctggctt taatgaggat ccattcgttt gtgaatatca aggccaatcg | 4920 |
| tctgacctgc ctcaacctcc tgtcaatgct ggcggcggct ctggtggtgg ttctggtggc | 4980 |
| ggctctgagg gtggtggctc tgagggtggc ggttctgagg gtggcggctc tgagggaggc | 5040 |
| ggttccggtg gtggctctgg ttccggtgat tttgattatg aaaagatggc aaacgctaat | 5100 |
| aagggggcta tgaccgaaaa tgccgatgaa aacgcgctac agtctgacgc taaaggcaaa | 5160 |
| cttgattctg tcgctactga ttacggtgct gctatcgatg gtttcattgg tgacgtttcc | 5220 |
| ggccttgcta atggtaatgg tgctactggt gattttgctg gctctaattc ccaaatggct | 5280 |
| caagtcggtg acggtgataa ttcaccttta atgaataatt tccgtcaata tttaccttcc | 5340 |
| ctccctcaat cggttgaatg tcgcccttt gtctttggcg ctggtaaacc atatgaattt | 5400 |
| tctattgatt gtgacaaaat aaacttattc cgtggtgtct ttgcgtttct tttatatgtt | 5460 |
| gccacctta tgtatgtatt ttctacgttt gctaacatac tgcgtaataa ggagtcttaa | 5520 |
| gcttggctct agaggtcga | 5539 |

<210> SEQ ID NO 46
<211> LENGTH: 17
<212> TYPE: PRT
<213> ORGANISM: Artificial Sequence
<220> FEATURE:
<223> OTHER INFORMATION: amino acid polymer

```
<400> SEQUENCE: 46

Gly Ala His Leu Ser Gln Arg Val Asp Tyr Lys Glu Tyr Lys Val Ser
1               5                   10                  15

Ile

<210> SEQ ID NO 47
<211> LENGTH: 17
<212> TYPE: PRT
<213> ORGANISM: Artificial Sequence
<220> FEATURE:
<223> OTHER INFORMATION: amino acid polymer

<400> SEQUENCE: 47

Gly Ala His Leu Ser Gln Arg Val Asp Tyr Lys Glu Tyr Lys Val Ser
1               5                   10                  15

Ile

<210> SEQ ID NO 48
<211> LENGTH: 18
<212> TYPE: PRT
<213> ORGANISM: Artificial Sequence
<220> FEATURE:
<223> OTHER INFORMATION: amino acid polymer

<400> SEQUENCE: 48

Gly Val Leu His Cys Asp Tyr Lys Glu Lys Ile Tyr Thr Gln Ser Ser
1               5                   10                  15

Ala Ser

<210> SEQ ID NO 49
<211> LENGTH: 18
<212> TYPE: PRT
<213> ORGANISM: Artificial Sequence
<220> FEATURE:
<223> OTHER INFORMATION: amino acid polymer

<400> SEQUENCE: 49

Gly Asn Gln Gln Cys Arg Gln Gln Leu Val Asp Tyr Lys Tyr Ser Ile
1               5                   10                  15

Tyr Ser

<210> SEQ ID NO 50
<211> LENGTH: 18
<212> TYPE: PRT
<213> ORGANISM: Artificial Sequence
<220> FEATURE:
<223> OTHER INFORMATION: amino acid polymer

<400> SEQUENCE: 50

Gly Pro Pro Pro Cys Ile Phe Tyr Ala Asp Tyr Lys Tyr Asn Glu Gly
1               5                   10                  15

Phe Ser

<210> SEQ ID NO 51
<211> LENGTH: 17
<212> TYPE: PRT
<213> ORGANISM: Artificial Sequence
<220> FEATURE:
<223> OTHER INFORMATION: amino acid polymer

<400> SEQUENCE: 51

Gly Tyr Arg Gln Ser Ile Gln Val Asp Tyr Lys Ile Arg Ser Glu Arg
```

```
<210> SEQ ID NO 52
<211> LENGTH: 19
<212> TYPE: PRT
<213> ORGANISM: Artificial Sequence
<220> FEATURE:
<223> OTHER INFORMATION: amino acid polymer

<400> SEQUENCE: 52

Gly Tyr Ser Trp Val Ser Glu Trp Gly Phe Ala Tyr Gln Val Asp Tyr
1               5                   10                  15

Lys Ile Ser

<210> SEQ ID NO 53
<211> LENGTH: 18
<212> TYPE: PRT
<213> ORGANISM: Artificial Sequence
<220> FEATURE:
<223> OTHER INFORMATION: amino acid polymer

<400> SEQUENCE: 53

Gly His Glu His Ser Trp Val Gln Ile Asp Tyr Lys Thr Ala Val Arg
1               5                   10                  15

Asp Ser

<210> SEQ ID NO 54
<211> LENGTH: 17
<212> TYPE: PRT
<213> ORGANISM: Artificial Sequence
<220> FEATURE:
<223> OTHER INFORMATION: amino acid polymer

<400> SEQUENCE: 54

Gly Phe Thr Met Ser Leu Glu Val Asp Tyr Lys Gln Lys Gln Gln Leu
1               5                   10                  15

Phe

<210> SEQ ID NO 55
<211> LENGTH: 18
<212> TYPE: PRT
<213> ORGANISM: Artificial Sequence
<220> FEATURE:
<223> OTHER INFORMATION: amino acid polymer

<400> SEQUENCE: 55

Gly Ile Glu Met Ser Ile Leu Glu Leu Val Asp Tyr Lys Ala Asn Leu
1               5                   10                  15

Tyr Ser

<210> SEQ ID NO 56
<211> LENGTH: 18
<212> TYPE: PRT
<213> ORGANISM: Artificial Sequence
<220> FEATURE:
<223> OTHER INFORMATION: amino acid polymer

<400> SEQUENCE: 56

Gly Glu Ala Pro Ser Tyr Gln Tyr Val Asp Tyr Lys Asn Ile Val Asp
1               5                   10                  15

Asn Ser
```

(preceding sequence, continued)
```
1               5                   10                  15

Phe
```

```
<210> SEQ ID NO 57
<211> LENGTH: 18
<212> TYPE: PRT
<213> ORGANISM: Artificial Sequence
<220> FEATURE:
<223> OTHER INFORMATION: amino acid polymer

<400> SEQUENCE: 57

Gly Glu Val Trp Ser Tyr Val Asp Tyr Lys Ser Pro Lys Lys Glu Pro
1               5                   10                  15

Ala Ser

<210> SEQ ID NO 58
<211> LENGTH: 18
<212> TYPE: PRT
<213> ORGANISM: Artificial Sequence
<220> FEATURE:
<223> OTHER INFORMATION: amino acid polymer

<400> SEQUENCE: 58

Gly Val Leu His Cys Asp Tyr Lys Phe Asn Leu Glu Tyr Pro Lys Pro
1               5                   10                  15

Asn Ser

<210> SEQ ID NO 59
<211> LENGTH: 19
<212> TYPE: PRT
<213> ORGANISM: Artificial Sequence
<220> FEATURE:
<223> OTHER INFORMATION: amino acid polymer

<400> SEQUENCE: 59

Gly Asp Tyr Arg Ser Trp Phe Val Tyr Leu Asp Tyr Lys His Lys Leu
1               5                   10                  15

Glu Ala Ser

<210> SEQ ID NO 60
<211> LENGTH: 18
<212> TYPE: PRT
<213> ORGANISM: Artificial Sequence
<220> FEATURE:
<223> OTHER INFORMATION: amino acid polymer

<400> SEQUENCE: 60

Gly Tyr Lys Trp Ser Glu Phe Gln Gln Ser Gln Gln Gly Ala Leu Phe
1               5                   10                  15

Ile Ser

<210> SEQ ID NO 61
<211> LENGTH: 18
<212> TYPE: PRT
<213> ORGANISM: Artificial Sequence
<220> FEATURE:
<223> OTHER INFORMATION: amino acid polymer

<400> SEQUENCE: 61

Gly Tyr Lys Trp Ser Glu Phe Gln Gln Ser Gln Gln Gly Ala Leu Phe
1               5                   10                  15

Ile Ser

<210> SEQ ID NO 62
<211> LENGTH: 18
<212> TYPE: PRT
```

```
<213> ORGANISM: Artificial Sequence
<220> FEATURE:
<223> OTHER INFORMATION: amino acid polymer

<400> SEQUENCE: 62

Gly Tyr Lys Trp Ser Glu Phe Gln His Phe Gly Gln Gln Gly Lys Tyr
1               5                   10                  15

Ala Ser

<210> SEQ ID NO 63
<211> LENGTH: 18
<212> TYPE: PRT
<213> ORGANISM: Artificial Sequence
<220> FEATURE:
<223> OTHER INFORMATION: amino acid polymer

<400> SEQUENCE: 63

Gly Tyr Lys Trp Ser Glu Phe Tyr Lys Asp Val Lys Gln Gln Glu Gly
1               5                   10                  15

Ala Ser

<210> SEQ ID NO 64
<211> LENGTH: 18
<212> TYPE: PRT
<213> ORGANISM: Artificial Sequence
<220> FEATURE:
<223> OTHER INFORMATION: amino acid polymer

<400> SEQUENCE: 64

Gly Tyr Lys Trp Ser Glu Phe Val Gln Glu Glu Lys Lys Val Asn Lys
1               5                   10                  15

Asp Ser

<210> SEQ ID NO 65
<211> LENGTH: 18
<212> TYPE: PRT
<213> ORGANISM: Artificial Sequence
<220> FEATURE:
<223> OTHER INFORMATION: amino acid polymer

<400> SEQUENCE: 65

Gly Tyr Lys Trp Ser Glu Phe His Asn Gln Phe Pro Gly Val Gln Asp
1               5                   10                  15

Phe Ser

<210> SEQ ID NO 66
<211> LENGTH: 18
<212> TYPE: PRT
<213> ORGANISM: Artificial Sequence
<220> FEATURE:
<223> OTHER INFORMATION: amino acid polymer

<400> SEQUENCE: 66

Gly Tyr Lys Trp Ser Glu Thr Trp Arg Gln Val Glu Asn Phe Gln His
1               5                   10                  15

Ala Ser

<210> SEQ ID NO 67
<211> LENGTH: 18
<212> TYPE: PRT
<213> ORGANISM: Artificial Sequence
<220> FEATURE:
<223> OTHER INFORMATION: amino acid polymer
```

```
<400> SEQUENCE: 67

Gly Tyr Lys Trp Ser Glu Thr Thr His Ser Val Gln Val Glu Ala His
1               5                   10                  15

Ala Ser

<210> SEQ ID NO 68
<211> LENGTH: 18
<212> TYPE: PRT
<213> ORGANISM: Artificial Sequence
<220> FEATURE:
<223> OTHER INFORMATION: amino acid polymer

<400> SEQUENCE: 68

Gly Tyr Lys Trp Ser Glu Ile His Thr Val Phe Glu Ala Ala Gln Val
1               5                   10                  15

Tyr Ser

<210> SEQ ID NO 69
<211> LENGTH: 17
<212> TYPE: PRT
<213> ORGANISM: Artificial Sequence
<220> FEATURE:
<223> OTHER INFORMATION: amino acid polymer

<400> SEQUENCE: 69

Gly Tyr Lys Trp Ser Glu Leu Tyr Gln Val Glu Arg Asp Gln Tyr Phe
1               5                   10                  15

Ser

<210> SEQ ID NO 70
<211> LENGTH: 18
<212> TYPE: PRT
<213> ORGANISM: Artificial Sequence
<220> FEATURE:
<223> OTHER INFORMATION: amino acid polymer

<400> SEQUENCE: 70

Gly Tyr Lys Trp Ser Glu Tyr Leu Ile Gly Lys Pro His Phe Glu His
1               5                   10                  15

Asp Ser

<210> SEQ ID NO 71
<211> LENGTH: 18
<212> TYPE: PRT
<213> ORGANISM: Artificial Sequence
<220> FEATURE:
<223> OTHER INFORMATION: amino acid polymer

<400> SEQUENCE: 71

Gly Tyr Lys Trp Ser Gln Tyr His Arg Glu Asp Lys Leu Val Gln Glu
1               5                   10                  15

Ile Ser

<210> SEQ ID NO 72
<211> LENGTH: 18
<212> TYPE: PRT
<213> ORGANISM: Artificial Sequence
<220> FEATURE:
<223> OTHER INFORMATION: amino acid polymer

<400> SEQUENCE: 72

Gly Tyr Lys Trp Ser Gln Tyr His Arg Glu Asp Lys Leu Val Gln Glu
1               5                   10                  15
```

Ile Ser

<210> SEQ ID NO 73
<211> LENGTH: 18
<212> TYPE: PRT
<213> ORGANISM: Artificial Sequence
<220> FEATURE:
<223> OTHER INFORMATION: amino acid polymer

<400> SEQUENCE: 73

Gly Tyr Lys Trp Ser Gln Trp His Asp Pro Ser Lys Glu Ala Ala Tyr
1               5                   10                  15

Asp Ser

<210> SEQ ID NO 74
<211> LENGTH: 18
<212> TYPE: PRT
<213> ORGANISM: Artificial Sequence
<220> FEATURE:
<223> OTHER INFORMATION: amino acid polymer

<400> SEQUENCE: 74

Gly Tyr Lys Trp Ser Leu Phe His Lys Ser Glu Glu Gln Val Asp Glu
1               5                   10                  15

Tyr Ser

<210> SEQ ID NO 75
<211> LENGTH: 18
<212> TYPE: PRT
<213> ORGANISM: Artificial Sequence
<220> FEATURE:
<223> OTHER INFORMATION: amino acid polymer

<400> SEQUENCE: 75

Gly Tyr Lys Trp Ser Leu Trp Leu Ser Glu Leu Lys Gln Gln Asn Glu
1               5                   10                  15

Ala Ser

<210> SEQ ID NO 76
<211> LENGTH: 18
<212> TYPE: PRT
<213> ORGANISM: Artificial Sequence
<220> FEATURE:
<223> OTHER INFORMATION: amino acid polymer

<400> SEQUENCE: 76

Gly Tyr Lys Trp Ser Ala Ile Asn Pro Lys Ile Gln Gln Asn Gln Asp
1               5                   10                  15

Phe Ser

<210> SEQ ID NO 77
<211> LENGTH: 19
<212> TYPE: PRT
<213> ORGANISM: Artificial Sequence
<220> FEATURE:
<223> OTHER INFORMATION: amino acid polymer

<400> SEQUENCE: 77

Gly Tyr Lys Trp Asn Ser Phe Asn Ser Trp Ser Gln Tyr Val Pro Glu
1               5                   10                  15

Pro Ile Ser

```
<210> SEQ ID NO 78
<211> LENGTH: 19
<212> TYPE: PRT
<213> ORGANISM: Artificial Sequence
<220> FEATURE:
<223> OTHER INFORMATION: amino acid polymer

<400> SEQUENCE: 78

Gly Tyr Lys Trp Asn Ser Phe Asn Ser Trp Ser Gln Tyr Val Pro Glu
1               5                   10                  15

Pro Ile Ser

<210> SEQ ID NO 79
<211> LENGTH: 18
<212> TYPE: PRT
<213> ORGANISM: Artificial Sequence
<220> FEATURE:
<223> OTHER INFORMATION: amino acid polymer

<400> SEQUENCE: 79

Gly Tyr Lys Trp Cys Leu Val Asn Gln Val Gln Cys Asn Glu Gln Arg
1               5                   10                  15

Ala Ser

<210> SEQ ID NO 80
<211> LENGTH: 19
<212> TYPE: PRT
<213> ORGANISM: Artificial Sequence
<220> FEATURE:
<223> OTHER INFORMATION: amino acid polymer

<400> SEQUENCE: 80

Gly Tyr Lys Trp Gln Ser Phe Gln His Asn Ala Glu Gln His Arg His
1               5                   10                  15

Pro Tyr Ser

<210> SEQ ID NO 81
<211> LENGTH: 18
<212> TYPE: PRT
<213> ORGANISM: Artificial Sequence
<220> FEATURE:
<223> OTHER INFORMATION: amino acid polymer

<400> SEQUENCE: 81

Gly Tyr Lys Phe Ser Glu Ile Leu Arg Leu Asp Tyr His Asp Leu Val
1               5                   10                  15

Asn Ser

<210> SEQ ID NO 82
<211> LENGTH: 18
<212> TYPE: PRT
<213> ORGANISM: Artificial Sequence
<220> FEATURE:
<223> OTHER INFORMATION: amino acid polymer

<400> SEQUENCE: 82

Gly Tyr Lys Phe Ser Glu Ile Leu Arg Leu Asp Tyr His Asp Leu Val
1               5                   10                  15

Asn Ser

<210> SEQ ID NO 83
<211> LENGTH: 18
<212> TYPE: PRT
<213> ORGANISM: Artificial Sequence
```

```
<220> FEATURE:
<223> OTHER INFORMATION: amino acid polymer

<400> SEQUENCE: 83

Gly Tyr Lys Phe Ser Glu Ile Phe Ser Val Tyr Gly Tyr Glu Pro His
1               5                   10                  15
Ala Ser

<210> SEQ ID NO 84
<211> LENGTH: 18
<212> TYPE: PRT
<213> ORGANISM: Artificial Sequence
<220> FEATURE:
<223> OTHER INFORMATION: amino acid polymer

<400> SEQUENCE: 84

Gly Tyr Lys Phe Ser Glu Trp Phe Gln Ile Ser Gln Ala Asp Gln Pro
1               5                   10                  15
Asp Ser

<210> SEQ ID NO 85
<211> LENGTH: 18
<212> TYPE: PRT
<213> ORGANISM: Artificial Sequence
<220> FEATURE:
<223> OTHER INFORMATION: amino acid polymer

<400> SEQUENCE: 85

Gly Tyr Lys Phe Ser Glu Leu Gln Thr Arg Ala Tyr Gln Pro Ala Val
1               5                   10                  15
Asp Ser

<210> SEQ ID NO 86
<211> LENGTH: 10
<212> TYPE: PRT
<213> ORGANISM: Artificial Sequence
<220> FEATURE:
<223> OTHER INFORMATION: amino acid polymer

<400> SEQUENCE: 86

Gly Tyr Lys Gln Lys Leu Tyr Phe Ala Ser
1               5                   10

<210> SEQ ID NO 87
<211> LENGTH: 10
<212> TYPE: PRT
<213> ORGANISM: Artificial Sequence
<220> FEATURE:
<223> OTHER INFORMATION: amino acid polymer

<400> SEQUENCE: 87

Gly Tyr Lys Gln Lys Leu Tyr Phe Ala Ser
1               5                   10

<210> SEQ ID NO 88
<211> LENGTH: 18
<212> TYPE: PRT
<213> ORGANISM: Artificial Sequence
<220> FEATURE:
<223> OTHER INFORMATION: amino acid polymer

<400> SEQUENCE: 88

Gly Gln His Val Ser Val Val Gln Val Gly Tyr Lys Gln Lys Glu Leu
1               5                   10                  15
```

Asn Ser

<210> SEQ ID NO 89
<211> LENGTH: 18
<212> TYPE: PRT
<213> ORGANISM: Artificial Sequence
<220> FEATURE:
<223> OTHER INFORMATION: amino acid polymer

<400> SEQUENCE: 89

Gly Tyr Lys Leu Ser Glu Leu Gln Ser Lys Thr Tyr Phe Phe Pro His
1               5                   10                  15

Phe Ser

<210> SEQ ID NO 90
<211> LENGTH: 18
<212> TYPE: PRT
<213> ORGANISM: Artificial Sequence
<220> FEATURE:
<223> OTHER INFORMATION: amino acid polymer

<400> SEQUENCE: 90

Gly Ala Pro Ala Ser Arg Gly Tyr Lys His Lys Glu Tyr Val Arg Lys
1               5                   10                  15

Cys Ser

<210> SEQ ID NO 91
<211> LENGTH: 18
<212> TYPE: PRT
<213> ORGANISM: Artificial Sequence
<220> FEATURE:
<223> OTHER INFORMATION: amino acid polymer

<400> SEQUENCE: 91

Gly Val Gln Ser Ser Lys Gly Tyr Lys Ala Lys Glu Gln Phe Asn Lys
1               5                   10                  15

Ala Ser

<210> SEQ ID NO 92
<211> LENGTH: 18
<212> TYPE: PRT
<213> ORGANISM: Artificial Sequence
<220> FEATURE:
<223> OTHER INFORMATION: amino acid polymer

<400> SEQUENCE: 92

Gly His Phe His Ser Glu Val Ser Tyr Lys Leu Lys Glu Leu Ile Ile
1               5                   10                  15

Tyr Ser

<210> SEQ ID NO 93
<211> LENGTH: 18
<212> TYPE: PRT
<213> ORGANISM: Artificial Sequence
<220> FEATURE:
<223> OTHER INFORMATION: amino acid polymer

<400> SEQUENCE: 93

Gly Val Trp Val Ser Asn Asn Trp Gly Pro His Gln Ser Gln Gln Thr
1               5                   10                  15

Asn Ser

<210> SEQ ID NO 94

```
<211> LENGTH: 18
<212> TYPE: PRT
<213> ORGANISM: Artificial Sequence
<220> FEATURE:
<223> OTHER INFORMATION: amino acid polymer

<400> SEQUENCE: 94

Gly Gln Phe Phe Ser Thr Asn Asp Ser His Asp Tyr Lys Asp Glu Asp
1               5                   10                  15

Ala Ser

<210> SEQ ID NO 95
<211> LENGTH: 17
<212> TYPE: PRT
<213> ORGANISM: Artificial Sequence
<220> FEATURE:
<223> OTHER INFORMATION: amino acid polymer

<400> SEQUENCE: 95

Gly Pro Glu Val Ser Asp Tyr Lys Asp Glu Asp Pro Phe Pro Tyr Phe
1               5                   10                  15

Ser

<210> SEQ ID NO 96
<211> LENGTH: 19
<212> TYPE: PRT
<213> ORGANISM: Artificial Sequence
<220> FEATURE:
<223> OTHER INFORMATION: amino acid polymer

<400> SEQUENCE: 96

Gly Leu Glu Ser Arg Ser Asp Asn Phe Ile Asp Tyr Lys Asp Leu Asp
1               5                   10                  15

Glu Asp Ser

<210> SEQ ID NO 97
<211> LENGTH: 17
<212> TYPE: PRT
<213> ORGANISM: Artificial Sequence
<220> FEATURE:
<223> OTHER INFORMATION: amino acid polymer

<400> SEQUENCE: 97

Gly Asn Gln Gly Ser Trp Trp Gln Asp Tyr Lys Gln Asp Asp Glu Phe
1               5                   10                  15

Ser

<210> SEQ ID NO 98
<211> LENGTH: 18
<212> TYPE: PRT
<213> ORGANISM: Artificial Sequence
<220> FEATURE:
<223> OTHER INFORMATION: amino acid polymer

<400> SEQUENCE: 98

Gly Pro Asp Pro Ser Asn Arg Asp Tyr Lys Asp Trp Asp Val Phe Ser
1               5                   10                  15

Ala Ser

<210> SEQ ID NO 99
<211> LENGTH: 18
<212> TYPE: PRT
<213> ORGANISM: Artificial Sequence
<220> FEATURE:
```

<223> OTHER INFORMATION: amino acid polymer

<400> SEQUENCE: 99

Gly His Gln Val Cys Asn Tyr Asp Phe Asp Tyr Lys Asp Ala Asp Lys
1               5                   10                  15

Asn Ser

<210> SEQ ID NO 100
<211> LENGTH: 18
<212> TYPE: PRT
<213> ORGANISM: Artificial Sequence
<220> FEATURE:
<223> OTHER INFORMATION: amino acid polymer

<400> SEQUENCE: 100

Gly Asn Pro Arg Ser Ala Glu Val Tyr Asn Asp Tyr Lys Glu Gln Asp
1               5                   10                  15

Ile Ser

<210> SEQ ID NO 101
<211> LENGTH: 19
<212> TYPE: PRT
<213> ORGANISM: Artificial Sequence
<220> FEATURE:
<223> OTHER INFORMATION: amino acid polymer

<400> SEQUENCE: 101

Gly Glu Glu Asn Cys Glu His Asn Asp Tyr Lys Glu Cys Asp Asn Ser
1               5                   10                  15

Tyr Tyr Ser

<210> SEQ ID NO 102
<211> LENGTH: 19
<212> TYPE: PRT
<213> ORGANISM: Artificial Sequence
<220> FEATURE:
<223> OTHER INFORMATION: amico acid polymer

<400> SEQUENCE: 102

Gly Glu Glu Asn Cys Glu His Asn Asp Tyr Lys Glu Cys Asp Asn Ser
1               5                   10                  15

Tyr Tyr Ser

<210> SEQ ID NO 103
<211> LENGTH: 19
<212> TYPE: PRT
<213> ORGANISM: Artificial Sequence
<220> FEATURE:
<223> OTHER INFORMATION: amino acid polymer

<400> SEQUENCE: 103

Gly Glu Glu Asn Cys Glu His Asn Asp Tyr Lys Glu Cys Asp Asn Ser
1               5                   10                  15

Tyr Tyr Ser

<210> SEQ ID NO 104
<211> LENGTH: 18
<212> TYPE: PRT
<213> ORGANISM: Artificial Sequence
<220> FEATURE:
<223> OTHER INFORMATION: amino acid polymer

<400> SEQUENCE: 104

Gly Val Phe Pro Ser Val Ile Phe Glu Asp Tyr Lys Glu Ser Asp Gly
1               5                   10                  15

Asp Ser

<210> SEQ ID NO 105
<211> LENGTH: 18
<212> TYPE: PRT
<213> ORGANISM: Artificial Sequence
<220> FEATURE:
<223> OTHER INFORMATION: amino acid polymer

<400> SEQUENCE: 105

Gly Tyr Glu Gln Ser Lys Gln Pro Asp Tyr Lys Trp Glu Asp Asp His
1               5                   10                  15

Phe Ser

<210> SEQ ID NO 106
<211> LENGTH: 18
<212> TYPE: PRT
<213> ORGANISM: Artificial Sequence
<220> FEATURE:
<223> OTHER INFORMATION: amino acid polymer

<400> SEQUENCE: 106

Gly Gly Thr Val Cys Trp Leu Arg Asp Tyr Lys Trp Glu Asp Glu His
1               5                   10                  15

Phe Ser

<210> SEQ ID NO 107
<211> LENGTH: 18
<212> TYPE: PRT
<213> ORGANISM: Artificial Sequence
<220> FEATURE:
<223> OTHER INFORMATION: amino acid polymer

<400> SEQUENCE: 107

Gly Gly Gln His Ser Glu Lys Asp Asp Tyr Lys Trp Glu Asp Val Arg
1               5                   10                  15

Cys Ser

<210> SEQ ID NO 108
<211> LENGTH: 18
<212> TYPE: PRT
<213> ORGANISM: Artificial Sequence
<220> FEATURE:
<223> OTHER INFORMATION: amino acid polymer

<400> SEQUENCE: 108

Gly Phe Asn Gln Ser Gly Phe Asp Tyr Lys Ile Trp Asp Glu Gln Arg
1               5                   10                  15

Ile Ser

<210> SEQ ID NO 109
<211> LENGTH: 18
<212> TYPE: PRT
<213> ORGANISM: Artificial Sequence
<220> FEATURE:
<223> OTHER INFORMATION: amino acid polymer

<400> SEQUENCE: 109

Gly Val Ser Gly Cys Tyr Phe Asp Tyr Lys Asn Cys Asp Glu Thr Pro
1               5                   10                  15

Asp Ser

<210> SEQ ID NO 110
<211> LENGTH: 18
<212> TYPE: PRT
<213> ORGANISM: Artificial Sequence
<220> FEATURE:
<223> OTHER INFORMATION: amino acid polymer

<400> SEQUENCE: 110

Gly His Ser Trp Ser Glu Ala Ile Asp Tyr Lys Trp Gln Asp Ile Arg
1               5                   10                  15

Asp Ser

<210> SEQ ID NO 111
<211> LENGTH: 18
<212> TYPE: PRT
<213> ORGANISM: Artificial Sequence
<220> FEATURE:
<223> OTHER INFORMATION: amino acid polymer

<400> SEQUENCE: 111

Gly Pro Phe Trp Ser Thr Trp Val Ala Val His Asp Tyr Lys Tyr Glu
1               5                   10                  15

Asp Ser

<210> SEQ ID NO 112
<211> LENGTH: 18
<212> TYPE: PRT
<213> ORGANISM: Artificial Sequence
<220> FEATURE:
<223> OTHER INFORMATION: amino acid polymer

<400> SEQUENCE: 112

Gly Asn Arg Gln Cys Tyr Leu Asp Tyr Lys Tyr Glu Asp His Asn Ala
1               5                   10                  15

Ala Ser

<210> SEQ ID NO 113
<211> LENGTH: 18
<212> TYPE: PRT
<213> ORGANISM: Artificial Sequence
<220> FEATURE:
<223> OTHER INFORMATION: amino acid polymer

<400> SEQUENCE: 113

Gly Asp Asp Trp Ser Asn Tyr Leu Asp Tyr Lys Leu Glu Asp Arg
1               5                   10                  15

Tyr Ser

<210> SEQ ID NO 114
<211> LENGTH: 18
<212> TYPE: PRT
<213> ORGANISM: Artificial Sequence
<220> FEATURE:
<223> OTHER INFORMATION: amino acid polymer

<400> SEQUENCE: 114

Gly Gly Ser Gln Ser His His Glu Ala Asp Tyr Lys Leu Glu Asp Thr
1               5                   10                  15

Tyr Ser

<210> SEQ ID NO 115
<211> LENGTH: 18

<210> SEQ ID NO 115
<211> LENGTH: (not shown)
<212> TYPE: PRT
<213> ORGANISM: Artificial Sequence
<220> FEATURE:
<223> OTHER INFORMATION: amino acid polymer

<400> SEQUENCE: 115

Gly Gly Asn Thr Ser Trp Tyr Glu His Asp Tyr Lys Phe Glu Asp Gln
1               5                   10                  15
Ala Ser

<210> SEQ ID NO 116
<211> LENGTH: 18
<212> TYPE: PRT
<213> ORGANISM: Artificial Sequence
<220> FEATURE:
<223> OTHER INFORMATION: amino acid polymer

<400> SEQUENCE: 116

Gly His Gln Asn Ser Gln Trp Ala Trp Asp Tyr Lys His Glu Asp Thr
1               5                   10                  15
Phe Ser

<210> SEQ ID NO 117
<211> LENGTH: 18
<212> TYPE: PRT
<213> ORGANISM: Artificial Sequence
<220> FEATURE:
<223> OTHER INFORMATION: amino acid polymer

<400> SEQUENCE: 117

Gly Phe Val Val Ser Pro Tyr Asp Tyr Lys Ser Glu Asp Thr Ala Cys
1               5                   10                  15
Phe Ser

<210> SEQ ID NO 118
<211> LENGTH: 18
<212> TYPE: PRT
<213> ORGANISM: Artificial Sequence
<220> FEATURE:
<223> OTHER INFORMATION: amino acid polymer

<400> SEQUENCE: 118

Gly Ala Asn Gln Ser Thr Asp Ala Tyr Val Asp Tyr Lys Leu Leu Asp
1               5                   10                  15
Tyr Ser

<210> SEQ ID NO 119
<211> LENGTH: 18
<212> TYPE: PRT
<213> ORGANISM: Artificial Sequence
<220> FEATURE:
<223> OTHER INFORMATION: amino acid polymer

<400> SEQUENCE: 119

Gly Ala Asn Gln Ser Thr Asp Ala Tyr Val Asp Tyr Lys Leu Leu Asp
1               5                   10                  15
Tyr Ser

<210> SEQ ID NO 120
<211> LENGTH: 18
<212> TYPE: PRT
<213> ORGANISM: Artificial Sequence
<220> FEATURE:
<223> OTHER INFORMATION: amino acid polymer

```
<400> SEQUENCE: 120

Gly His Trp Gln Ser Ala Phe Asp Pro Asp Tyr Lys Leu Thr Asp Thr
1               5                   10                  15

Ala Ser

<210> SEQ ID NO 121
<211> LENGTH: 18
<212> TYPE: PRT
<213> ORGANISM: Artificial Sequence
<220> FEATURE:
<223> OTHER INFORMATION: amino acid polymer

<400> SEQUENCE: 121

Gly Thr Val Trp Ser Asp Gly Trp Ser Val Asp Tyr Lys Leu Ala Asp
1               5                   10                  15

Tyr Ser

<210> SEQ ID NO 122
<211> LENGTH: 18
<212> TYPE: PRT
<213> ORGANISM: Artificial Sequence
<220> FEATURE:
<223> OTHER INFORMATION: amino acid polymer

<400> SEQUENCE: 122

Gly Asn Ile His Ser Asp Tyr Lys Leu Tyr Asp Gly Thr His Ala Thr
1               5                   10                  15

Asp Ser

<210> SEQ ID NO 123
<211> LENGTH: 18
<212> TYPE: PRT
<213> ORGANISM: Artificial Sequence
<220> FEATURE:
<223> OTHER INFORMATION: amino acid polymer

<400> SEQUENCE: 123

Gly Ser Leu His Ser Ile Trp His Gln Glu Asp Tyr Lys Leu Gln Asp
1               5                   10                  15

Phe Ser

<210> SEQ ID NO 124
<211> LENGTH: 18
<212> TYPE: PRT
<213> ORGANISM: Artificial Sequence
<220> FEATURE:
<223> OTHER INFORMATION: amino acid polymer

<400> SEQUENCE: 124

Gly Asp Gly Trp Ser Lys Tyr Phe Glu Asp Tyr Lys Asn Cys Asp Thr
1               5                   10                  15

Tyr Ser

<210> SEQ ID NO 125
<211> LENGTH: 18
<212> TYPE: PRT
<213> ORGANISM: Artificial Sequence
<220> FEATURE:
<223> OTHER INFORMATION: amino acid polymer

<400> SEQUENCE: 125

Gly Glu Val Ser Ser Ile Gln His Trp Asp Tyr Lys Asn Tyr Asp Pro
```

```
1               5                   10                  15

Asn Ser

<210> SEQ ID NO 126
<211> LENGTH: 18
<212> TYPE: PRT
<213> ORGANISM: Artificial Sequence
<220> FEATURE:
<223> OTHER INFORMATION: amino acid polymer

<400> SEQUENCE: 126

Gly Pro Ser Thr Ser Trp Asn Ser Asp Asp Tyr Lys Phe Gly Asp Val
1               5                   10                  15

Asp Ser

<210> SEQ ID NO 127
<211> LENGTH: 18
<212> TYPE: PRT
<213> ORGANISM: Artificial Sequence
<220> FEATURE:
<223> OTHER INFORMATION: amino acid polymer

<400> SEQUENCE: 127

Gly Leu Pro Val Cys Gly Glu Glu Leu Gly Ile Asp Tyr Lys Phe Tyr
1               5                   10                  15

Asp Ser

<210> SEQ ID NO 128
<211> LENGTH: 18
<212> TYPE: PRT
<213> ORGANISM: Artificial Sequence
<220> FEATURE:
<223> OTHER INFORMATION: amino acid polymer

<400> SEQUENCE: 128

Gly Gln Ser Thr Cys Asp Asp Pro Trp Asp Tyr Lys Cys Cys Asp Gly
1               5                   10                  15

Asn Ser

<210> SEQ ID NO 129
<211> LENGTH: 19
<212> TYPE: PRT
<213> ORGANISM: Artificial Sequence
<220> FEATURE:
<223> OTHER INFORMATION: amino acid polymer

<400> SEQUENCE: 129

Gly Phe Leu Ala Ser Lys Trp Gly His Phe Glu Lys Asp Tyr Lys Cys
1               5                   10                  15

Tyr Asp Ser

<210> SEQ ID NO 130
<211> LENGTH: 18
<212> TYPE: PRT
<213> ORGANISM: Artificial Sequence
<220> FEATURE:
<223> OTHER INFORMATION: amino acid polymer

<400> SEQUENCE: 130

Gly His Val Leu Ser Asp Asp Phe Val Asp Tyr Lys Gln Pro Asp Leu
1               5                   10                  15

Tyr Ser
```

```
<210> SEQ ID NO 131
<211> LENGTH: 18
<212> TYPE: PRT
<213> ORGANISM: Artificial Sequence
<220> FEATURE:
<223> OTHER INFORMATION: amino acid polymer

<400> SEQUENCE: 131

Gly Ser Leu Ala Cys Asp Tyr Lys Gln Tyr Asp Pro Glu Val Val Arg
1               5                   10                  15

Asn Ser

<210> SEQ ID NO 132
<211> LENGTH: 18
<212> TYPE: PRT
<213> ORGANISM: Artificial Sequence
<220> FEATURE:
<223> OTHER INFORMATION: amino acid polymer

<400> SEQUENCE: 132

Gly Glu Leu His Cys Phe Gly Glu Asn His Asp Tyr Lys Ser Ala Asp
1               5                   10                  15

Ile Ser

<210> SEQ ID NO 133
<211> LENGTH: 17
<212> TYPE: PRT
<213> ORGANISM: Artificial Sequence
<220> FEATURE:
<223> OTHER INFORMATION: amino acid polymer

<400> SEQUENCE: 133

Gly Gly Arg Val Cys Ser Tyr Gln Asp Asp Tyr Lys Ser Cys Glu Tyr
1               5                   10                  15

Ser

<210> SEQ ID NO 134
<211> LENGTH: 18
<212> TYPE: PRT
<213> ORGANISM: Artificial Sequence
<220> FEATURE:
<223> OTHER INFORMATION: amino acid polymer

<400> SEQUENCE: 134

Gly Ile Thr Leu Cys Ala Phe His Asp Tyr Arg Trp Asp Asp Ile Gln
1               5                   10                  15

Ala Ser

<210> SEQ ID NO 135
<211> LENGTH: 18
<212> TYPE: PRT
<213> ORGANISM: Artificial Sequence
<220> FEATURE:
<223> OTHER INFORMATION: amino acid polymer

<400> SEQUENCE: 135

Gly Gln Phe Ser Ser Asp Tyr Gln Ile Ser Asp Tyr Lys Glu Leu Asp
1               5                   10                  15

Tyr Ser

<210> SEQ ID NO 136
<211> LENGTH: 18
<212> TYPE: PRT
```

<213> ORGANISM: Artificial Sequence
<220> FEATURE:
<223> OTHER INFORMATION: amino acid polymer

<400> SEQUENCE: 136

Gly Lys Pro His Ser Asp Tyr Val Tyr Asn Asp Cys Lys Gln Glu Asp
1               5                   10                  15

Ile Ser

<210> SEQ ID NO 137
<211> LENGTH: 18
<212> TYPE: PRT
<213> ORGANISM: Artificial Sequence
<220> FEATURE:
<223> OTHER INFORMATION: amino acid polymer

<400> SEQUENCE: 137

Gly Ser Pro Pro Cys Gly Trp Glu Ala Ile Gln Glu Tyr Lys Leu Cys
1               5                   10                  15

Asp Ser

<210> SEQ ID NO 138
<211> LENGTH: 18
<212> TYPE: PRT
<213> ORGANISM: Artificial Sequence
<220> FEATURE:
<223> OTHER INFORMATION: amino acid polymer

<400> SEQUENCE: 138

Gly Asn Gln Gly Cys Tyr Lys Leu Trp Pro Glu Cys Tyr Ser Val Tyr
1               5                   10                  15

Asn Ser

<210> SEQ ID NO 139
<211> LENGTH: 19
<212> TYPE: PRT
<213> ORGANISM: Artificial Sequence
<220> FEATURE:
<223> OTHER INFORMATION: amino acid polymer

<400> SEQUENCE: 139

Gly Ala Gly Tyr Gly Cys Tyr Leu Phe Tyr Glu Ile Trp Tyr Phe Gly
1               5                   10                  15

Cys Cys Ser

<210> SEQ ID NO 140
<211> LENGTH: 18
<212> TYPE: PRT
<213> ORGANISM: Artificial Sequence
<220> FEATURE:
<223> OTHER INFORMATION: amino acid polymer

<400> SEQUENCE: 140

Gly Val Pro Pro Cys Asn Ser Glu Asp Lys Tyr Cys Ile Asp Gln Phe
1               5                   10                  15

Ala Ser

<210> SEQ ID NO 141
<211> LENGTH: 18
<212> TYPE: PRT
<213> ORGANISM: Artificial Sequence
<220> FEATURE:
<223> OTHER INFORMATION: amino acid polymer -continued

```
<400> SEQUENCE: 141

Gly Gln Tyr Thr Cys Ala Trp Gln Trp Leu Leu Tyr Gln Leu Cys Ile
1               5                   10                  15

Phe Ser

<210> SEQ ID NO 142
<211> LENGTH: 8
<212> TYPE: PRT
<213> ORGANISM: Artificial Sequence
<220> FEATURE:
<223> OTHER INFORMATION: amino acid polymer
<220> FEATURE:
<223> OTHER INFORMATION: Flag-Tag

<400> SEQUENCE: 142

Asp Tyr Lys Asp Asp Asp Asp Lys
1               5
```